(12) United States Patent
Fernandez-Valdivia

(10) Patent No.: US 12,359,265 B2
(45) Date of Patent: Jul. 15, 2025

(54) SYSTEMS AND METHODS FOR ULTRA-SPECIFIC AND ULTRA-SENSITIVE NUCLEIC ACID DETECTION

(71) Applicant: Wayne State University, Detroit, MI (US)

(72) Inventor: Rodrigo Fernandez-Valdivia, Bloomfield Hills, MI (US)

(73) Assignee: Wayne State University, Detroit, MI (US)

( * ) Notice: Subject to any disclaimer, the term of this patent is extended or adjusted under 35 U.S.C. 154(b) by 932 days.

(21) Appl. No.: 17/512,246

(22) Filed: Oct. 27, 2021

(65) Prior Publication Data

US 2022/0127658 A1   Apr. 28, 2022

Related U.S. Application Data

(60) Provisional application No. 63/106,106, filed on Oct. 27, 2020.

(51) Int. Cl.
| | | |
|---|---|---|
| *C12Q 1/70* | (2006.01) | |
| *C12N 9/22* | (2006.01) | |
| *C12Q 1/686* | (2018.01) | |

(52) U.S. Cl.
CPC ............. *C12Q 1/70* (2013.01); *C12N 9/22* (2013.01); *C12Q 1/686* (2013.01); *G01N 2800/26* (2013.01)

(58) Field of Classification Search
None
See application file for complete search history.

(56) References Cited

PUBLICATIONS

Yang et al., J. Clin. Microbiol., 2002, 40(9):3449-3454 (Year: 2002).*
Sun et al., BioTechniques, 2014, 56:319-325 (Year: 2014).*
Zhong et al., Lap Chip, 2011, 11, 2167, 8 pages (Year: 2011).*

* cited by examiner

*Primary Examiner* — Stacy B Chen
(74) *Attorney, Agent, or Firm* — Julie K. Staple; Fishman Stewart PLLC

(57) ABSTRACT

Methods according to aspects of the disclosure, compositions and kits therefore, include at least one, two, or three sets of amplification primers and hydrolysis probes with at least two separate corresponding readouts per set. According to aspects of the present disclosure, the at least two hydrolysis probes and associated pair of primers of each set are directed to opposite strands of an amplification product of the set. According to aspects of the present disclosure, one of the two hydrolysis probes in each set is directed to a first strand of the amplification product and therefore has a sequence complementary to the first strand of the amplification product and the second of the two hydrolysis probes in the set is directed to the second strand of the amplification product and therefore has a sequence complementary to the second strand of the amplification product.

5 Claims, 11 Drawing Sheets

Specification includes a Sequence Listing.

```
┌─────────────────────────────────────────────────────────────────────┐
│ forming a first reaction mixture, the first reaction mixture        │
│ comprising the test sample, nucleic acid amplification reagents,    │
│ and a first set of amplification primers and hydrolysis probes,     │
│ the first set comprising: a first hydrolysis probe specific for     │
│ the target nucleic acid, a second hydrolysis probe specific for     │
│ the target nucleic acid, and a pair of amplification primers        │
│ specific for the target nucleic acid, wherein the first hydrolysis  │
│ probe comprises a first fluorophore and a quencher of the first     │
│ fluorophore, wherein the second hydrolysis probe comprises a        │
│ second fluorophore and a quencher of the second fluorophore, and    │
│ wherein the first hydrolysis probe and the second hydrolysis probe  │
│ are specific for an amplification product of the first pair of      │
│ amplification primers                                               │
│                                                                 102 │
└─────────────────────────────────────────────────────────────────────┘
                                    ↓
┌─────────────────────────────────────────────────────────────────────┐
│ reacting the first reaction mixture under amplification conditions, │
│ producing a first amplification product when the target nucleic     │
│ acid is present in the test sample, wherein detectable signals are  │
│ generated by the first and second fluorophores released from the    │
│ hydrolysis probes                                                   │
│                                                                 104 │
└─────────────────────────────────────────────────────────────────────┘
                                    ↓
┌─────────────────────────────────────────────────────────────────────┐
│ detecting the detectable signals of the fluorophores released from  │
│ the hydrolysis probes                                               │
│                                                                 106 │
└─────────────────────────────────────────────────────────────────────┘
                                    ↓
┌─────────────────────────────────────────────────────────────────────┐
│ calculating a cycle threshold (Ct) value for the first fluorophore  │
│ and the second fluorophore while reacting the first reaction        │
│ mixture                                                             │
│                                                                 108 │
└─────────────────────────────────────────────────────────────────────┘
                                    ↓
┌─────────────────────────────────────────────────────────────────────┐
│ determining that the test sample contains the target nucleic acid   │
│ when the Ct value: 1) of the first fluorophore and the second       │
│ fluorophore of the first reaction mixture is positive and less than │
│ a predetermined value                                               │
│                                                                 110 │
└─────────────────────────────────────────────────────────────────────┘
```

FIG. 11

SEQUENCE LISTING

<160> NUMBER OF SEQ ID NOS: 17

<210> SEQ ID NO 1
<211> LENGTH: 22
<212> TYPE: DNA
<213> ORGANISM: Betacoronavirus severe acute respiratory syndrome-
      related coronavirus

<400> SEQUENCE: 1
gtggaccctc agattcaact gg                                              22

<210> SEQ ID NO 2
<211> LENGTH: 21
<212> TYPE: DNA
<213> ORGANISM: Betacoronavirus severe acute respiratory syndrome-
      related coronavirus

<400> SEQUENCE: 2
tgagagcggt gaaccaagac g                                               21

<210> SEQ ID NO 3
<211> LENGTH: 25
<212> TYPE: DNA
<213> ORGANISM: Betacoronavirus severe acute respiratory syndrome-
      related coronavirus

<400> SEQUENCE: 3
gtaaccagaa tggagaacgc agtgg                                           25

<210> SEQ ID NO 4
<211> LENGTH: 23
<212> TYPE: DNA
<213> ORGANISM: Betacoronavirus severe acute respiratory syndrome-
      related coronavirus

<400> SEQUENCE: 4
ggtaaacctt ggggccgacg ttg                                             23

<210> SEQ ID NO 5
<211> LENGTH: 24
<212> TYPE: DNA
<213> ORGANISM: Betacoronavirus severe acute respiratory syndrome-
      related coronavirus

<400> SEQUENCE: 5
ctgctaacaa tgctgcaatc gtgc                                            24

<210> SEQ ID NO 6
<211> LENGTH: 22
<212> TYPE: DNA
<213> ORGANISM: Betacoronavirus severe acute respiratory syndrome-
      related coronavirus

<400> SEQUENCE: 6
ctgttgcgac tacgtgatga gg                                              22

<210> SEQ ID NO 7
<211> LENGTH: 24
<212> TYPE: DNA
<213> ORGANISM: Betacoronavirus severe acute respiratory syndrome-
      related coronavirus

<400> SEQUENCE: 7
gcttctacgc agaagggagc agag                                            24

<210> SEQ ID NO 8
<211> LENGTH: 21
<212> TYPE: DNA
<213> ORGANISM: Betacoronavirus severe acute respiratory syndrome-
      related coronavirus

<400> SEQUENCE: 8
cgagaagagg cttgactgcc g                                               21

<210> SEQ ID NO 9
<211> LENGTH: 22
<212> TYPE: DNA
<213> ORGANISM: Betacoronavirus severe acute respiratory syndrome-
      related coronavirus

<400> SEQUENCE: 9
gctctcactc aacatggcaa gg                                              22

<210> SEQ ID NO 10
<211> LENGTH: 23
<212> TYPE: DNA
<213> ORGANISM: Betacoronavirus severe acute respiratory syndrome-
      related coronavirus

<400> SEQUENCE: 10
cgaattcgtc tggtagctct tcg                                             23

<210> SEQ ID NO 11
<211> LENGTH: 22
<212> TYPE: DNA
<213> ORGANISM: Betacoronavirus severe acute respiratory syndrome-
      related coronavirus

<400> SEQUENCE: 11
cctcgaggac aaggcgttcc aa                                              22

<210> SEQ ID NO 12
<211> LENGTH: 25
<212> TYPE: DNA
<213> ORGANISM: Betacoronavirus severe acute respiratory syndrome-
      related coronavirus

<400> SEQUENCE: 12
ggtcatctgg actgctattg gtgtt                                           25

<210> SEQ ID NO 13
<211> LENGTH: 19
<212> TYPE: DNA
<213> ORGANISM: Homo sapiens

<400> SEQUENCE: 13
cagatttgga cctgcgagc                                                  19

<210> SEQ ID NO 14
<211> LENGTH: 20
<212> TYPE: DNA
<213> ORGANISM: Homo sapiens

<400> SEQUENCE: 14
agcggctgtc tccacaagtc                                                 20

<210> SEQ ID NO 15
<211> LENGTH: 23
<212> TYPE: DNA

```
<213> ORGANISM: Homo sapiens

<400> SEQUENCE: 15
ttctgacctg aaggctctgc gcg                                           23

<210> SEQ ID NO 16
<211> LENGTH: 25
<212> TYPE: DNA
<213> ORGANISM: Homo sapiens

<400> SEQUENCE: 16
gattgatagc aacaactgaa tagcc                                         25

<210> SEQ ID NO 17
<211> LENGTH: 20
<212> TYPE: DNA
<213> ORGANISM: Homo sapiens

<400> SEQUENCE: 17
gcggctgtct ccacaagtcc                                               20
```

SYSTEMS AND METHODS FOR ULTRA-SPECIFIC AND ULTRA-SENSITIVE NUCLEIC ACID DETECTION

REFERENCE TO RELATED APPLICATION

This application claims priority from U.S. Provisional Patent Application Ser. No. 63/106,106, filed Oct. 27, 2020, the entire content of which is incorporated herein by reference.

FIELD OF THE INVENTION

The present disclosure relates generally to systems and methods for detection of a target nucleic acid. In particular aspects, the present disclosure relates to highly specific and sensitive systems and methods for detection of a target nucleic acid.

BACKGROUND OF THE INVENTION

Detection of nucleic acids is required and useful in many applications, such as forensics, food analysis, medical diagnosis, and medical screening.

Currently, the Covid-19 pandemic and SARS-CoV-2 spread is a global problem critically requiring high-throughput testing for symptomatic and asymptomatic patients as well as systematized probing for viral contamination in biological and non-biological specimens. However, current molecular detection systems use standard materials and methods, such as those of the WHO and CDC, that may underperform in terms of specificity and detection limits.

Furthermore, development and establishment of early and highly-reliable surveillance systems to robustly assess viral shedding and spreading to provide the necessary information required to implement control and mitigation measures for the rapidly impending Covid-19 waves is required.

Therefore, there is an urgent need for systems and methods useful to detect very low copy numbers of nucleic acids in an ultra-specific manner.

The present disclosure provides a highly-advanced, multi-array and multispectral molecular detection system that allows ultra-specific detection of target nucleic acids, even in low copy number, with marked effective elimination of both false positives and false negatives.

Methods according to aspects of the present disclosure utilize sets of primers and hydrolysis-based probes, FRET-based noise cancellation, and mathematical/algorithmic biconditional logical connectives analysis, providing ultra-specific and ultra-sensitive detection of nucleic acids.

SUMMARY OF THE INVENTION

Methods of detecting a target nucleic acid in a test sample including or suspected of including the target nucleic acid are provided according to aspects of the present disclosure which include: detecting the presence of the target nucleic acid in the test sample by quantitative polymerase chain reaction (qPCR), wherein the qPCR includes one, two, or three of i), ii), and iii): i) forming a first reaction mixture, the first reaction mixture including the test sample, nucleic acid amplification reagents, and a first set of amplification primers and hydrolysis probes, the first set including: a first hydrolysis probe specific for the target nucleic acid, a second hydrolysis probe specific for the target nucleic acid, and a pair of amplification primers specific for the target nucleic acid, wherein the first hydrolysis probe includes a first fluorophore and a quencher of the first fluorophore, wherein the second hydrolysis probe includes a second fluorophore and a quencher of the second fluorophore, and wherein the first hydrolysis probe and the second hydrolysis probe are specific for an amplification product of the first pair of amplification primers; ii) forming a second reaction mixture, the second reaction mixture including the test sample, nucleic acid amplification reagents, and a second set of amplification primers and hydrolysis probes, the second set including: a third hydrolysis probe specific for the target nucleic acid, a fourth hydrolysis probe specific for the target nucleic acid, and a second pair of amplification primers specific for the target nucleic acid, wherein the third hydrolysis probe includes a third fluorophore and a quencher of the third fluorophore, and wherein the fourth hydrolysis probe includes a fourth fluorophore and a quencher of the fourth fluorophore, and wherein the third hydrolysis probe and the fourth hydrolysis probe are specific for an amplification product of the second pair of amplification primers; iii) forming a third reaction mixture, the third reaction mixture including the test sample, nucleic acid amplification reagents, and a third set of amplification primers and hydrolysis probes, the third set including: a fifth hydrolysis probe specific for the target nucleic acid, a sixth hydrolysis probe specific for the target nucleic acid, and a pair of amplification primers specific for the target nucleic acid, wherein the fifth hydrolysis probe includes a fifth fluorophore and a quencher of the fifth fluorophore, and wherein the sixth hydrolysis probe includes a sixth fluorophore and a quencher of the sixth fluorophore, and wherein the fifth hydrolysis probe and the sixth hydrolysis probe are specific for an amplification product of the third pair of amplification primers; reacting the reaction mixtures under amplification conditions, producing first, second, and third amplification products when the target nucleic acid is present in the test sample, wherein detectable signals are generated by the first, second, third, fourth, fifth, and sixth fluorophores released from the hydrolysis probes; detecting the detectable signals of the fluorophores released from the hydrolysis probes; calculating a cycle threshold (Ct) value for the first fluorophore and the second fluorophore while reacting the first reaction mixture; calculating a Ct value for the third fluorophore and the fourth fluorophore while reacting the second reaction mixture; calculating a Ct value for the fifth fluorophore and the sixth fluorophore while reacting the third reaction mixture; and determining that the test sample contains the target nucleic acid when the Ct value: 1) of the first fluorophore and the second fluorophore of the first reaction mixture is positive and less than a predetermined value; 2) of the third fluorophore and the fourth fluorophore of the second reaction mixture is positive and less than a predetermined value; and 3) of the fifth fluorophore and the sixth fluorophore of the third reaction mixture is positive and less than a predetermined value. According to aspects of the present disclosure, methods of detecting a target nucleic acid in a test sample further include a control. According to aspects of the present disclosure, the control includes: forming a fourth reaction mixture, the fourth reaction mixture including the test sample, nucleic acid amplification reagents, and a fourth set of amplification primers and at least one hydrolysis probe, the fourth set including: a seventh hydrolysis probe, and a pair of primers specific for the control nucleic acid, wherein the seventh hydrolysis probe includes a seventh fluorophore and a quencher of the seventh fluorophore.

According to aspects of the present disclosure, the control includes including a fourth set of amplification primers and at least one control hydrolysis probe in at least one of the first, second, or third reaction mixtures, the fourth set including: a seventh hydrolysis probe, and a pair of primers specific for the control nucleic acid, wherein the seventh hydrolysis probe includes a seventh fluorophore and a quencher of the seventh fluorophore.

According to aspects of the present disclosure, the amplification product of the first pair of amplification primers is a double stranded DNA molecule which has a first strand complementary to a second strand, wherein the first hydrolysis probe is complementary to a first region of the first strand and the second hydrolysis probe is complementary to a first region of the second strand, wherein the first region of the first strand and the first region of the second strand are not complementary to each other, and wherein the first hydrolysis probe and second hydrolysis probe are not complementary to each other.

According to aspects of the present disclosure, the amplification product of the second pair of amplification primers is a double stranded DNA molecule which has a first strand complementary to a second strand, wherein the third hydrolysis probe is complementary to a first region of the first strand of the amplification product of the second pair of amplification primers and the fourth hydrolysis probe is complementary to a first region of the second strand of the amplification product of the second pair of amplification primers.

According to aspects of the present disclosure, the amplification product of the third pair of amplification primers is a double stranded DNA molecule which has a first strand complementary to a second strand, wherein the fifth hydrolysis probe is complementary to a first region of the first strand of the amplification product of the third pair of amplification primers and the sixth hydrolysis probe is complementary to a first region of the second strand of the amplification product of the third pair of amplification primers.

Amplification primers and hydrolysis probes included in methods according to aspects of the present disclosure are at least "substantially complementary" having at least 85% complementarity to a target sequence, or at least 86%, 87%, 88%, 89%, 90%, 91%, 92%, 93%, 94%, 95%, 96%, 97%, 98%, 99%, or greater, complementarity to a target nucleic acid sequence.

Methods of detecting intact severe acute respiratory syndrome coronavirus 2 (SARS-CoV-2) in a test sample including or suspected of including SARS-CoV-2 are provided according to aspects of the present disclosure which include: detecting the presence of a SARS-CoV-2 nucleic acid in the test sample by reverse-transcription quantitative polymerase chain reaction (RT-qPCR), wherein the RT-qPCR includes: forming a reaction mixture including the test sample, nucleic acid amplification reagents, and one, two, or three of i), ii), and iii): i) a first set of amplification primers and hydrolysis probes, the first set including: a first hydrolysis probe specific for the target nucleic acid, a second hydrolysis probe specific for the target nucleic acid, and a first pair of amplification primers specific for the target nucleic acid, wherein the first hydrolysis probe includes a first fluorophore and a quencher of the first fluorophore, wherein the second hydrolysis probe includes a second fluorophore and a quencher of the second fluorophore, and wherein the first hydrolysis probe and the second hydrolysis probe are specific for an amplification product of the first pair of amplification primers; ii) a second set of amplification primers and hydrolysis probes, the second set including: a third hydrolysis probe specific for the target nucleic acid, a fourth hydrolysis probe specific for the target nucleic acid, and a second pair of amplification primers specific for the target nucleic acid, wherein the third hydrolysis probe includes a third fluorophore and a quencher of the third fluorophore, wherein the fourth hydrolysis probe includes a fourth fluorophore and a quencher of the fourth fluorophore, and wherein the third hydrolysis probe and the fourth hydrolysis probe are specific for an amplification product of the second pair of amplification primers; iii) a third set of amplification primers and hydrolysis probes, the third set including: a fifth hydrolysis probe specific for the target nucleic acid, a sixth hydrolysis probe specific for the target nucleic acid, and a third pair of amplification primers specific for the target nucleic acid, wherein the fifth hydrolysis probe includes a fifth fluorophore and a quencher of the fifth fluorophore, wherein the sixth hydrolysis probe includes a sixth fluorophore and a quencher of the sixth fluorophore, and wherein the fifth hydrolysis probe and the sixth hydrolysis probe are specific for an amplification product of the third pair of amplification primers; reacting the reaction mixture under amplification conditions, producing one, two, or more of: first, second, and third amplification products when the target nucleic acid is present in the test sample, wherein detectable signals are generated by the fluorophores released from the hydrolysis probes; detecting the detectable signals of the fluorophores released from the hydrolysis probes; calculating a cycle threshold (Ct) value for fluorophores while reacting the reaction mixture; and determining that the test sample contains the target nucleic acid when the Ct value for all of the fluorophores is positive and less than a predetermined value. According to aspects of the present disclosure, methods of detecting a target nucleic acid in a test sample further include a control. According to aspects of the present disclosure, methods of detecting a target nucleic acid in a test sample further include a control, wherein the reaction mixture further includes at least one control hydrolysis probe, and a pair of control primers, wherein the control hydrolysis probe and control primers are specific for a non-target nucleic acid, wherein the control hydrolysis probe includes a control fluorophore and a quencher of the control fluorophore.

According to aspects of the present disclosure, methods of detecting a target nucleic acid in a test sample further include a control, wherein the control includes: forming a further reaction mixture, the further reaction mixture including the test sample, nucleic acid amplification reagents, at least one control hydrolysis probe, and a pair of control primers, wherein the control hydrolysis probe and control primers are specific for a non-target nucleic acid, wherein the control hydrolysis probe includes a control fluorophore and a quencher of the control fluorophore.

Methods of detecting intact severe acute respiratory syndrome coronavirus 2 (SARS-CoV-2) in a test sample including or suspected of including SARS-CoV-2 are provided according to aspects of the present disclosure which include: detecting the presence of a SARS-CoV-2 nucleic acid encoding nucleocapsid phosphoprotein in the test sample by reverse-transcription quantitative polymerase chain reaction (RT-qPCR), wherein the RT-qPCR includes: forming a reaction mixture including the test sample, nucleic acid amplification reagents, and one, two, or three of i), ii), and iii): i) a first set of amplification primers and hydrolysis probes, the first set including: a first hydrolysis probe including SEQ ID NO:3, a second hydrolysis probe including SEQ ID NO:4, and amplification primers including SEQ ID NO:1 and SEQ ID NO:2, wherein the first hydrolysis probe includes a first fluorophore and a quencher of the first fluorophore, wherein the second hydrolysis probe includes a second fluorophore and a quencher of the second fluorophore, and wherein the first hydrolysis probe and the second hydrolysis probe are specific for an amplification product of the amplification primers; ii) a second set of amplification primers and hydrolysis probes, the second set including: a third hydrolysis probe including SEQ ID NO:7, a fourth hydrolysis probe including SEQ ID NO:8, and amplification primers including SEQ ID NO:5 and SEQ ID NO:6, wherein the third hydrolysis probe includes a third fluorophore and a quencher of the third fluorophore, wherein the fourth hydrolysis probe includes a fourth fluorophore and a quencher of the fourth fluorophore, and wherein the third hydrolysis probe and the fourth hydrolysis probe are specific for an amplification product of the second pair of amplification primers; and iii) a third set of amplification primers and hydrolysis probes, the third set including: a fifth hydrolysis probe including SEQ ID NO:11, a sixth hydrolysis probe including SEQ ID NO:12, and amplification primers including SEQ ID NO:9 and SEQ ID NO:10, wherein the fifth hydrolysis probe includes a fifth fluorophore and a quencher of the fifth fluorophore, wherein the sixth hydrolysis probe includes a sixth fluorophore and a quencher of the sixth fluorophore, and wherein the fifth hydrolysis probe and the sixth hydrolysis probe are specific for an amplification product of the third pair of amplification primers; reacting the reaction mixture under amplification conditions, producing one, two, or more of: first, second, and third amplification products when the SARS-CoV-2 nucleic acid encoding nucleocapsid phosphoprotein is present in the test sample, wherein detectable signals are generated by the fluorophores released from the hydrolysis probes; detecting the detectable signals of the amplification products; calculating a cycle threshold (Ct) value for fluorophores while reacting the reaction mixture; and determining that the test sample contains SARS-CoV-2 when the Ct value for all of the fluorophores is positive, in the reaction or reactions performed, and none is negative, and less than a predetermined value. According to aspects of the present disclosure, neither human nucleic acids, nor nucleic acids of coronaviruses other than SARS-CoV-2, are amplified if present in the test sample. According to aspects of the present disclosure, methods of detecting a target nucleic acid in a test sample further include a control.

According to aspects of the present disclosure, methods of detecting a target SARS-CoV-2 nucleic acid in a test sample further include at least one control hydrolysis probe, and a pair of control primers, wherein the control hydrolysis probe and control primers are specific for a non-SARS-CoV-2 nucleic acid, wherein the control hydrolysis probe includes a control fluorophore and a quencher of the control fluorophore.

According to aspects of the present disclosure, methods of detecting a target SARS-CoV-2 nucleic acid in a test sample further include forming a further reaction mixture, the further reaction mixture including the test sample, nucleic acid amplification reagents, at least one control hydrolysis probe, and a pair of control primers, wherein the control hydrolysis probe and control primers are specific for a non-SARS-CoV-2 nucleic acid, wherein the control hydrolysis probe includes a control fluorophore and a quencher of the control fluorophore.

Methods of detecting intact severe acute respiratory syndrome coronavirus 2 (SARS-CoV-2) in a test sample including or suspected of including SARS-CoV-2 which include: detecting the presence of a SARS-CoV-2 nucleic acid encoding nucleocapsid phosphoprotein in the test sample by reverse-transcription quantitative polymerase chain reaction (RT-qPCR), wherein the RT-qPCR includes one, two, or three of i), ii), and iii): i) forming a first reaction mixture, the first reaction mixture including the test sample, nucleic acid amplification reagents, and a first set of amplification primers and hydrolysis probes, the first set including: a first hydrolysis probe including SEQ ID NO:3, a second hydrolysis probe including SEQ ID NO:4, and primers including SEQ ID NO:1 and SEQ ID NO:2, wherein the first hydrolysis probe includes a first fluorophore and a quencher of the first fluorophore, wherein the second hydrolysis probe includes a second fluorophore and a quencher of the second fluorophore, and wherein the first hydrolysis probe and the second hydrolysis probe are specific for an amplification product of the first pair of amplification primers; ii) forming a second reaction mixture, the second reaction mixture including the test sample, nucleic acid amplification reagents, and a second set of amplification primers and hydrolysis probes, the second set including: a third hydrolysis probe including SEQ ID NO:7, a fourth hydrolysis probe including SEQ ID NO:8, and primers including SEQ ID NO:5 and SEQ ID NO:6, wherein the third hydrolysis probe includes a third fluorophore and a quencher of the third fluorophore, wherein the fourth hydrolysis probe includes a fourth fluorophore and a quencher of the fourth fluorophore, and wherein the third hydrolysis probe and the fourth hydrolysis probe are specific for an amplification product of the second pair of amplification primers; iii) forming a third reaction mixture, the third reaction mixture including the test sample, nucleic acid amplification reagents, and a third set of amplification primers and hydrolysis probes, the third set including: a fifth hydrolysis probe including SEQ ID NO:11, a sixth hydrolysis probe including SEQ ID NO:12, and primers including SEQ ID NO:9 and SEQ ID NO:10, wherein the fifth hydrolysis probe includes a fifth fluorophore and a quencher of the fifth fluorophore, wherein the sixth hydrolysis probe includes a sixth fluorophore and a quencher of the sixth fluorophore, and wherein the fifth hydrolysis probe and the sixth hydrolysis probe are specific for an amplification product of the third pair of amplification primers; reacting the reaction mixtures under amplification conditions, producing first, and/or second, and/or third amplification products when the SARS-CoV-2 nucleic acid encoding nucleocapsid phosphoprotein is present in the test sample, wherein detectable signals are generated by the first and second and/or third and fourth; and/or fifth and sixth fluorophores released from the hydrolysis probes; detecting the detectable signals of the first, and/or second, and/or third, amplification products; calculating a cycle threshold (Ct) value for the first fluorophore and the second fluorophore while reacting the first reaction mixture; and/or calculating a Ct value for the third fluorophore and the fourth fluorophore while reacting the second reaction mixture; and/or calculating a Ct value for the fifth fluorophore and the sixth fluorophore while reacting the third reaction mixture; and determining that the test sample contains SARS-CoV-2 when the Ct value for one or more of: 1) the first fluorophore and the second fluorophore of the first reaction mixture; 2) the third fluorophore and the fourth fluorophore of the second reaction mixture; and 3) the fifth fluorophore and the sixth fluorophore of the third reaction mixture; is positive and none is negative, and the Ct value is less than a predetermined value. According to aspects of the present disclosure, neither human nucleic acids, nor nucleic acids of coronaviruses other than SARS-CoV-2, are amplified if present in the test sample. According to aspects of the present disclosure, methods of detecting a target nucleic acid in a test sample further include a control.

According to aspects of the present disclosure, methods of detecting a target SARS-CoV-2 nucleic acid in a test sample further include at least one control hydrolysis probe, and a pair of control primers, wherein the control hydrolysis probe and control primers are specific for a non-SARS-CoV-2 nucleic acid, wherein the control hydrolysis probe includes a control fluorophore and a quencher of the control fluorophore. According to aspects of the present disclosure, methods of detecting a target nucleic acid in a test sample further include a control, wherein the control includes: forming a fourth reaction mixture, the fourth reaction mixture including the test sample, nucleic acid amplification reagents, and a fourth set of amplification primers and at least one hydrolysis probe, the fourth set including: a seventh hydrolysis probe, and a pair of primers specific for a non-SARS-CoV-2 nucleic acid, wherein the seventh hydrolysis probe includes a seventh fluorophore and a quencher of the seventh fluorophore.

According to aspects of the present disclosure, methods of detecting a target nucleic acid in a test sample further include a control, wherein the control includes including a fourth set of amplification primers and at least one control hydrolysis probe in at least one of the first, second, or third reaction mixtures, the fourth set including: a seventh hydrolysis probe, and a pair of primers specific for a non-SARS-CoV-2 nucleic acid, wherein the seventh hydrolysis probe includes a seventh fluorophore and a quencher of the seventh fluorophore.

According to aspects of the present disclosure, the test sample is, or is derived from, a biological sample obtained from a mammalian subject.

According to aspects of the present disclosure, the test sample is, or is derived from, an environmental sample.

According to aspects of the present disclosure, the qPCR is reverse transcription qPCR (RT-qPCR).

According to aspects of the present disclosure, the qPCR is digital PCR (dPCR).

According to aspects of the present disclosure, dPCR is digital droplet PCR (ddPCR).

According to aspects of the present disclosure, the Ct value indicative of a positive result is less than 40.

According to aspects of the present disclosure, the emission maximum of the second fluorophore is distinguishable from the emission maximum of the first fluorophore, the emission maximum of the fourth fluorophore is distinguishable from the emission maximum of the third fluorophore, and the emission maximum of the sixth fluorophore is distinguishable from the emission maximum of the fifth fluorophore.

According to aspects of the present disclosure, each of the first fluorophore, second fluorophore, third fluorophore, fourth fluorophore, fifth fluorophore, and sixth fluorophore, when included in the reaction mixture, are detectably different in one or more emission characteristics.

According to aspects of the present disclosure, the first fluorophore is FAM or HEX, the second fluorophore is FAM or HEX but not identical to the first fluorophore, the quencher of the first fluorophore is Black Hole Quencher 1 (BHQ1), and the quencher of the second fluorophore is BHQ1; the third fluorophore is FAM or HEX, the fourth fluorophore is FAM or HEX but not identical to the third fluorophore, the quencher of the third fluorophore is BHQ1, and the quencher of the fourth fluorophore is BHQ1; and the fifth fluorophore is FAM or HEX, the sixth fluorophore is FAM or HEX but not identical to the fifth fluorophore, the quencher of the fifth fluorophore is BHQ1, and the quencher of the sixth fluorophore is BHQ1.

According to aspects of the present disclosure, the first, second, and third reaction mixtures each include a thermostable polymerase which has 5'→3' exonuclease activity.

According to aspects of the present disclosure, the thermostable polymerase which has 5'→3' exonuclease activity is a Taq or Tth polymerase.

According to aspects of the present disclosure, non-target nucleic acids are not significantly amplified if present in the test sample.

Compositions for detecting a target nucleic acid in a test sample including or suspected of including the target nucleic acid are provided according to aspects of the present disclosure which include at least a first set of amplification primers and hydrolysis probes specific for the target nucleic acid, the first set including a first hydrolysis probe, a second hydrolysis probe, and a first pair of amplification primers, wherein the first hydrolysis probe includes a first fluorophore and a quencher of the first fluorophore, wherein the second hydrolysis probe includes a second fluorophore and a quencher of the second fluorophore and wherein the first hydrolysis probe and the second hydrolysis probe are specific for an amplification product of the first pair of amplification primers. According to aspects of the present disclosure, the target nucleic acid is a SARS-CoV-2 nucleic acid.

Compositions for detecting a target nucleic acid in a test sample including or suspected of including the target nucleic acid are provided according to aspects of the present disclosure which further include a second set of amplification primers and hydrolysis probes specific for the target nucleic acid, the second set including a third hydrolysis probe, a fourth hydrolysis probe, and a second pair of amplification primers, wherein the third hydrolysis probe includes a third fluorophore and a quencher of the third fluorophore, wherein the fourth hydrolysis probe includes a fourth fluorophore and a quencher of the fourth fluorophore and wherein the third hydrolysis probe and the fourth hydrolysis probe are specific for an amplification product of the second pair of amplification primers. According to aspects of the present disclosure, the target nucleic acid is a SARS-CoV-2 nucleic acid.

Compositions for detecting a target nucleic acid in a test sample including or suspected of including the target nucleic acid are provided according to aspects of the present disclosure which further include a third set of amplification primers and hydrolysis probes specific for the target nucleic acid, the third set including a fifth hydrolysis probe, a sixth hydrolysis probe, and a third pair of amplification primers, wherein the fifth hydrolysis probe includes a fifth fluorophore and a quencher of the fifth fluorophore, wherein the sixth hydrolysis probe includes a sixth fluorophore and a quencher of the sixth fluorophore and wherein the fifth hydrolysis probe and the sixth hydrolysis probe are specific for an amplification product of the third pair of amplification primers. According to aspects of the present disclosure, the target nucleic acid is a SARS-CoV-2 nucleic acid.

According to aspects of the present disclosure, the first fluorophore and the second fluorophore included in the composition have detectably different emission maxima, different excitation maxima, or the same emission maxima and excitation maxima, the third fluorophore and the fourth fluorophore have detectably different emission maxima, different excitation maxima, or the same emission maxima and excitation maxima, and the fifth fluorophore and the sixth fluorophore have detectably different emission maxima, different excitation maxima, or the same emission maxima and excitation maxima.

Compositions for detecting a target nucleic acid in a test sample including or suspected of including the target nucleic acid are provided according to aspects of the present disclosure which further include a pair of control amplification primers and/or a control hydrolysis probe. Compositions for detecting a target nucleic acid in a test sample including or suspected of including the target nucleic acid are provided according to aspects of the present disclosure wherein the control hydrolysis probe includes a seventh fluorophore which has an excitation maximum and an emission maximum distinguishable from each of the first fluorophore, second fluorophore, third fluorophore, fourth fluorophore, fifth fluorophore, and sixth fluorophore or which has an excitation maximum and/or an emission maximum which is not distinguishable from at least one of the first fluorophore, second fluorophore, third fluorophore, fourth fluorophore, fifth fluorophore, and sixth fluorophore, or which has an excitation maximum and/or an emission maximum which is not distinguishable from any of: the first fluorophore, second fluorophore, third fluorophore, fourth fluorophore, fifth fluorophore, and sixth fluorophore. According to aspects of the present disclosure, the target nucleic acid is a SARS-CoV-2 nucleic acid.

Compositions for detecting a target nucleic acid in a test sample including or suspected of including the target nucleic acid are provided according to aspects of the present disclosure which further include one or more reverse transcription reagents, one or more hybridization reagents and/or one or more PCR reagents, such as, but not limited to, a reverse transcriptase, a thermostable polymerase with 5'→3' exonuclease activity, and/or a hybridization and/or polymerase buffer.

Commercial packages for detecting a target nucleic acid in a test sample including or suspected of including the target nucleic acid are provided according to aspects of the present disclosure which include at least a first set of amplification primers and hydrolysis probes specific for the target nucleic acid, the first set including a first hydrolysis probe, a second hydrolysis probe, and a first pair of amplification primers, wherein the first hydrolysis probe includes a first fluorophore and a quencher of the first fluorophore, wherein the second hydrolysis probe includes a second fluorophore and a quencher of the second fluorophore and wherein the first hydrolysis probe and the second hydrolysis probe are specific for an amplification product of the first pair of amplification primers. According to aspects of the present disclosure, the target nucleic acid is a SARS-CoV-2 nucleic acid.

Commercial packages for detecting a target nucleic acid in a test sample including or suspected of including the target nucleic acid are provided according to aspects of the present disclosure which further include a second set of amplification primers and hydrolysis probes specific for the target nucleic acid, the second set including a third hydrolysis probe, a fourth hydrolysis probe, and a second pair of amplification primers, wherein the third hydrolysis probe includes a third fluorophore and a quencher of the third fluorophore, wherein the fourth hydrolysis probe includes a fourth fluorophore and a quencher of the fourth fluorophore and wherein the third hydrolysis probe and the fourth hydrolysis probe are specific for an amplification product of the second pair of amplification primers. According to aspects of the present disclosure, the target nucleic acid is a SARS-CoV-2 nucleic acid.

Commercial packages for detecting a target nucleic acid in a test sample including or suspected of including the target nucleic acid are provided according to aspects of the present disclosure which further include a third set of amplification primers and hydrolysis probes specific for the target nucleic acid, the third set including a fifth hydrolysis probe, a sixth hydrolysis probe, and a third pair of amplification primers, wherein the fifth hydrolysis probe includes a fifth fluorophore and a quencher of the fifth fluorophore, wherein the sixth hydrolysis probe includes a sixth fluorophore and a quencher of the sixth fluorophore and wherein the fifth hydrolysis probe and the sixth hydrolysis probe are specific for an amplification product of the third pair of amplification primers. According to aspects of the present disclosure, the target nucleic acid is a SARS-CoV-2 nucleic acid.

According to aspects of the present disclosure, the first fluorophore and the second fluorophore included in the commercial package have detectably different emission maxima, different excitation maxima, or the same emission maxima and excitation maxima, the third fluorophore and the fourth fluorophore have detectably different emission maxima, different excitation maxima, or the same emission maxima and excitation maxima, and the fifth fluorophore and the sixth fluorophore have detectably different emission maxima, different excitation maxima, or the same emission maxima and excitation maxima.

Commercial packages for detecting a target nucleic acid in a test sample including or suspected of including the target nucleic acid are provided according to aspects of the present disclosure which further include a pair of control amplification primers and/or a control hydrolysis probe. Commercial packages for detecting a target nucleic acid in a test sample including or suspected of including the target nucleic acid are provided according to aspects of the present disclosure wherein the control hydrolysis probe includes a seventh fluorophore which has an excitation maximum and an emission maximum distinguishable from each of the first fluorophore, second fluorophore, third fluorophore, fourth fluorophore, fifth fluorophore, and sixth fluorophore or which has an excitation maximum and/or an emission maximum which is not distinguishable from at least one of the first fluorophore, second fluorophore, third fluorophore, fourth fluorophore, fifth fluorophore, and sixth fluorophore, or which has an excitation maximum and/or an emission maximum which is not distinguishable from any of: the first fluorophore, second fluorophore, third fluorophore, fourth fluorophore, fifth fluorophore, and sixth fluorophore. According to aspects of the present disclosure, the target nucleic acid is a SARS-CoV-2 nucleic acid.

Commercial packages for detecting a target nucleic acid in a test sample including or suspected of including the target nucleic acid are provided according to aspects of the present disclosure which further include one or more reverse transcription reagents, one or more hybridization reagents and/or one or more PCR reagents, such as, but not limited to, a reverse transcriptase, a thermostable polymerase with 5'→3' exonuclease activity, and/or a hybridization and/or polymerase buffer.

Methods of detecting a target nucleic acid in a test sample including or suspected of including the target nucleic acid are provided according to aspects of the present disclosure which include: detecting the presence of the target nucleic acid in the test sample by quantitative polymerase chain reaction (qPCR), wherein the qPCR includes: i) forming a first reaction mixture, the first reaction mixture including the test sample, nucleic acid amplification reagents, and a first set of amplification primers and hydrolysis probes, the first set including: a first hydrolysis probe specific for the target nucleic acid, a second hydrolysis probe specific for the target nucleic acid, and a pair of amplification primers specific for the target nucleic acid, wherein the first hydrolysis probe includes a first fluorophore and a quencher of the first fluorophore, wherein the second hydrolysis probe includes a second fluorophore and a quencher of the second fluorophore, and wherein the first hydrolysis probe and the second hydrolysis probe are specific for an amplification product of the first pair of amplification primers; reacting the first reaction mixture under amplification conditions, producing a first amplification product when the target nucleic acid is present in the test sample, wherein detectable signals are generated by the first and second fluorophores released from the hydrolysis probes; detecting the detectable signals of the fluorophores released from the hydrolysis probes; calculating a cycle threshold (Ct) value for the first fluorophore and the second fluorophore while reacting the first reaction mixture; and determining that the test sample contains the target nucleic acid when the Ct value: 1) of the first fluorophore and the second fluorophore of the first reaction mixture is positive and less than a predetermined value.

Methods of detecting a target nucleic acid in a test sample including or suspected of including the target nucleic acid are provided according to aspects of the present disclosure which further include: ii) forming a second reaction mixture, the second reaction mixture including the test sample, nucleic acid amplification reagents, and a second set of amplification primers and hydrolysis probes, the second set including: a third hydrolysis probe specific for the target nucleic acid, a fourth hydrolysis probe specific for the target nucleic acid, and a second pair of amplification primers specific for the target nucleic acid, wherein the third hydrolysis probe includes a third fluorophore and a quencher of the third fluorophore, and wherein the fourth hydrolysis probe includes a fourth fluorophore and a quencher of the fourth fluorophore, and wherein the third hydrolysis probe and the fourth hydrolysis probe are specific for an amplification product of the second pair of amplification primers; reacting the second reaction mixture under amplification conditions, producing a second amplification product when the target nucleic acid is present in the test sample, wherein detectable signals are generated by the third and fourth fluorophores released from the hydrolysis probes; detecting the detectable signals of the fluorophores released from the hydrolysis probes; calculating a cycle threshold (Ct) value for the third fluorophore and the fourth fluorophore while reacting the second reaction mixture; and determining that the test sample contains the target nucleic acid when the Ct value: 1) of the third fluorophore and the fourth fluorophore of the second reaction mixture is positive and less than a predetermined value.

Methods of detecting a target nucleic acid in a test sample including or suspected of including the target nucleic acid are provided according to aspects of the present disclosure which further include: iii) forming a third reaction mixture, the third reaction mixture including the test sample, nucleic acid amplification reagents, and a third set of amplification primers and hydrolysis probes, the third set including: a fifth hydrolysis probe specific for the target nucleic acid, a sixth hydrolysis probe specific for the target nucleic acid, and a pair of amplification primers specific for the target nucleic acid, wherein the fifth hydrolysis probe includes a fifth fluorophore and a quencher of the fifth fluorophore, and wherein the sixth hydrolysis probe includes a sixth fluorophore and a quencher of the sixth fluorophore, and wherein the fifth hydrolysis probe and the sixth hydrolysis probe are specific for an amplification product of the third pair of amplification primers; reacting the third reaction mixture under amplification conditions, producing a third amplification product when the target nucleic acid is present in the test sample, wherein detectable signals are generated by the fifth and sixth fluorophores released from the hydrolysis probes; detecting the detectable signals of the fluorophores released from the hydrolysis probes; calculating a cycle threshold (Ct) value for the fifth fluorophore and the sixth fluorophore while reacting the third reaction mixture; and determining that the test sample contains the target nucleic acid when the Ct value: 1) of the fifth fluorophore and the sixth fluorophore of the third reaction mixture is positive and less than a predetermined value.

According to aspects of the present disclosure, methods of detecting a target nucleic acid in a test sample further include a control. Methods of detecting a target nucleic acid in a test sample including or suspected of including the target nucleic acid are provided according to aspects of the present disclosure which further include: forming a fourth reaction mixture as a control, the fourth reaction mixture including the test sample, nucleic acid amplification reagents, and a fourth set of amplification primers and at least one hydrolysis probe, the fourth set including: a seventh hydrolysis probe, and a pair of primers specific for the control nucleic acid, wherein the seventh hydrolysis probe includes a seventh fluorophore and a quencher of the seventh fluorophore.

According to aspects of the present disclosure the control includes including a fourth set of amplification primers and at least one control hydrolysis probe in at least one of the first, second, or third reaction mixtures, the fourth set including: a seventh hydrolysis probe, and a pair of primers specific for the control nucleic acid, wherein the seventh hydrolysis probe includes a seventh fluorophore and a quencher of the seventh fluorophore.

BRIEF DESCRIPTION OF THE DRAWINGS

As illustrated in FIG. 10, according to aspects of the present disclosure, the at least two hydrolysis probes are complementary to opposite strands of an amplification product. As further illustrated in FIG. 10, according to aspects of the present disclosure, one hydrolysis probe 40 is complementary to a region of the first strand 20 of the amplification product and the second hydrolysis probe 50 is complementary to a region of the second strand 30 of the amplification product; and FIG. 11 is a schematic illustration of methods according to aspects of the present disclosure including steps 102, 104, 106, 108, and 110.

DETAILED DESCRIPTION OF THE INVENTION

Figure 1A:
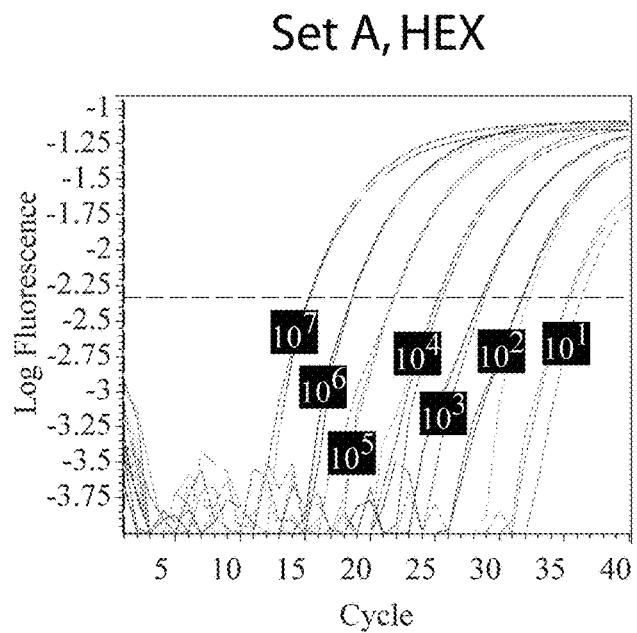
FIG. 1A is a graph showing representative traces demonstrating highly-reliable and high-precision SARS-CoV-2 detection using primers/probes Set A and indicating effective amplification and detection of 10^7 to 10^1 SARS-CoV-2 nucleocapsid RNA in HEX channel.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; and Herdewijn, P. (Ed.), Oligonucleotide Synthesis: Methods and Applications, Methods in Molecular Biology, Humana Press, 2004.

The singular terms "a," "an," and "the" are not intended to be limiting and include plural referents unless explicitly stated otherwise or the context clearly indicates otherwise.

Methods according to aspects of the disclosure include at least one, two, or three sets of amplification primers and hydrolysis probes with at least two separate corresponding readouts per set, wherein the amplification primers and hydrolysis probes are specific for highly-conserved segments of a target nucleic acid. Methods for SARS-CoV-2 according to aspects of the present disclosure detect as little as 1 copy/µL of a target nucleic acid per sample.

According to aspects of the present disclosure, the at least two hydrolysis probes and associated pair of primers are directed to opposite strands of an amplification product. According to aspects of the present disclosure, one of the two hydrolysis probes is directed to a first strand of the amplification product and therefore has a sequence complementary to the first strand of the amplification product and the second of the two hydrolysis probes is directed to the second strand of the amplification product and therefore has a sequence complementary to the second strand of the amplification product.

The term "nucleic acid" as used herein refers to RNA or DNA molecules having more than one nucleotide in any form including single-stranded, double-stranded, oligonucleotide or polynucleotide.

Methods of detecting a target nucleic acid in a test sample including or suspected of including the nucleic acid, are provided according to aspects of the present disclosure which include: detecting the presence of the target nucleic acid in the test sample by quantitative polymerase chain reaction (qPCR), wherein the qPCR includes: i) forming a first reaction mixture including the test sample, nucleic acid amplification reagents, and a first set of amplification primers and hydrolysis probes, the first set including: a first hydrolysis probe specific for the target nucleic acid, a second hydrolysis probe specific for the target nucleic acid, and a first pair of amplification primers specific for the target nucleic acid, wherein the first hydrolysis probe includes a first fluorophore and a quencher of the first fluorophore, wherein the second hydrolysis probe includes a second fluorophore and a quencher of the second fluorophore, and wherein the first hydrolysis probe and the second hydrolysis probe are specific for an amplification product of the first pair of amplification primers. Methods of detecting a target nucleic acid in a test sample including or suspected of including the nucleic acid, are provided according to aspects of the present disclosure which include: detecting the presence of the target nucleic acid in the test sample by quantitative polymerase chain reaction (qPCR), wherein the qPCR further includes ii) forming a second reaction mixture including the test sample, nucleic acid amplification reagents, and a second set of amplification primers and hydrolysis probes, the second set including: a third hydrolysis probe specific for the target nucleic acid, a fourth hydrolysis probe specific for the target nucleic acid, and a second pair of amplification primers specific for the target nucleic acid, wherein the third hydrolysis probe includes a third fluorophore and a quencher of the third fluorophore, wherein the fourth hydrolysis probe includes a fourth fluorophore and a quencher of the fourth fluorophore, and wherein the third hydrolysis probe and the fourth hydrolysis probe are specific for an amplification product of the second pair of amplification primers. Methods of detecting a target nucleic acid in a test sample including or suspected of including the nucleic acid, are provided according to aspects of the present disclosure which include: detecting the presence of the target nucleic acid in the test sample by quantitative polymerase chain reaction (qPCR), wherein the qPCR further includes iii) forming a third reaction mixture including the test sample, nucleic acid amplification reagents, and a third set of amplification primers and hydrolysis probes, the third set including: a fifth hydrolysis probe specific for the target nucleic acid, a sixth hydrolysis probe specific for the target nucleic acid, and a third pair of amplification primers specific for the target nucleic acid, wherein the fifth hydrolysis probe includes a fifth fluorophore and a quencher of the fifth fluorophore, wherein the sixth hydrolysis probe includes a sixth fluorophore and a quencher of the sixth fluorophore, and wherein the fifth hydrolysis probe and the sixth hydrolysis probe are specific for an amplification product of the third pair of amplification primers.

Methods of detecting a target nucleic acid in a test sample including or suspected of including the nucleic acid, are provided according to aspects of the present disclosure which include: detecting the presence of the target nucleic acid in the test sample by quantitative polymerase chain reaction (qPCR), wherein the qPCR includes:
  i) forming a first reaction mixture including the test sample, nucleic acid amplification reagents, and a first set of amplification primers and hydrolysis probes, the first set including: a first hydrolysis probe specific for the target nucleic acid, a second hydrolysis probe specific for the target nucleic acid, and a first pair of amplification primers specific for the target nucleic acid, wherein the first hydrolysis probe includes a first fluorophore and a quencher of the first fluorophore, wherein the second hydrolysis probe includes a second fluorophore and a quencher of the second fluorophore, and wherein the first hydrolysis probe and the second hydrolysis probe are specific for an amplification product of the first pair of amplification primers;
  ii) forming a second reaction mixture including the test sample, nucleic acid amplification reagents, and a second set of amplification primers and hydrolysis probes, the second set including: a third hydrolysis probe specific for the target nucleic acid, a fourth hydrolysis probe specific for the target nucleic acid, and a second pair of amplification primers specific for the target nucleic acid, wherein the third hydrolysis probe includes a third fluorophore and a quencher of the third fluorophore, wherein the fourth hydrolysis probe includes a fourth fluorophore and a quencher of the fourth fluorophore, and wherein the third hydrolysis probe and the fourth hydrolysis probe are specific for an amplification product of the second pair of amplification primers; and
  iii) forming a third reaction mixture including the test sample, nucleic acid amplification reagents, and a third set of amplification primers and hydrolysis probes, the third set including: a fifth hydrolysis probe specific for the target nucleic acid, a sixth hydrolysis probe specific for the target nucleic acid, and a third pair of amplification primers specific for the target nucleic acid, wherein the fifth hydrolysis probe includes a fifth fluorophore and a quencher of the fifth fluorophore, wherein the sixth hydrolysis probe includes a sixth fluorophore and a quencher of the sixth fluorophore, and wherein the fifth hydrolysis probe and the sixth hydrolysis probe are specific for an amplification product of the third pair of amplification primers.

Any two or more of the reaction mixtures may be separate or together, i.e. multiplexed.

According to aspects of the present disclosure, the first fluorophore and the second fluorophore are different from each other and have distinguishable emission maxima, the third fluorophore and the fourth fluorophore are different from each other and have distinguishable emission maxima, and the fifth fluorophore and the sixth fluorophore are different from each other and have distinguishable emission maxima.

According to aspects of the present disclosure, the first fluorophore and the second fluorophore are the same or have indistinguishable emission maxima, the third fluorophore and the fourth fluorophore are the same or have indistinguishable emission maxima, and the fifth fluorophore and the sixth fluorophore are the same or have indistinguishable emission maxima.

According to aspects of the present disclosure, all of the first fluorophore, the second fluorophore, the third fluorophore, the fourth fluorophore, the fifth fluorophore and the sixth fluorophore, are the same or have indistinguishable emission maxima.

According to aspects of the present disclosure, the first fluorophore and the second fluorophore have different excitation maxima and different or indistinguishable emission maxima, the third fluorophore and the fourth fluorophore have different excitation maxima and different or indistinguishable emission maxima, and the fifth fluorophore and the sixth fluorophore have different excitation maxima and different or indistinguishable emission maxima.

According to aspects of the present disclosure, all of the first fluorophore, the second fluorophore, the third fluorophore, the fourth fluorophore, the fifth fluorophore and the sixth fluorophore, have different excitation maxima and different or indistinguishable emission maxima.

Methods, compositions, and commercial packages, for detecting a target nucleic acid in a test sample including or suspected of including the nucleic acid, are provided according to aspects of the present disclosure including one, two, or three reaction mixtures with one, two, or three sets of amplification primers and hydrolysis probes. The present disclosure is not limited with respect to the number of reaction mixtures and corresponding sets of amplification primers and hydrolysis probes, and likewise is not limited with respect to whether such reaction mixtures are separate or multiplexed. Thus, four, five, six, or more reaction mixtures and corresponding sets of amplification primers and hydrolysis probes may be included.

Methods, compositions, and commercial packages according to aspects of the present disclosure include three sets of amplification primers and hydrolysis probes specific for the target nucleic acid, wherein each set includes two hydrolysis probes and one pair of amplification primers, wherein the two hydrolysis probes specifically hybridize to the negative and positive strands, respectively, of an amplicon generated by amplification of the target nucleic acid using the amplification primers, and wherein the two hydrolysis probes specifically hybridize to two non-overlapping sequences of the amplicon.

Optionally, the reaction mixture, or reaction mixtures, contain a reverse transcriptase such that the qPCR is RT-qPCR and the reaction mixture, or reaction mixtures, are reacted under reverse transcription reaction conditions to produce target cDNA from a target RNA in the test sample. Alternatively, the reverse transcription reaction is performed prior to generating the reaction mixtures, thereby generating target cDNA from target RNA in the test sample.

In a further option, the qPCR and/or RT-PCR includes digital PCR (dPCR). In a still further option, the dPCR is digital droplet PCR (ddPCR).

Methods according to aspects of the present disclosure further include reacting the reaction mixture under amplification conditions, producing at least a first amplification product when the target nucleic acid is present in the test sample, wherein detectable signals are generated by the fluorophores released from the hydrolysis probes.

Methods according to aspects of the present disclosure further include reacting the reaction mixtures under amplification conditions, producing at least first and second amplification products when the target nucleic acid is present in the test sample, wherein detectable signals are generated by the fluorophores released from the hydrolysis probes.

Methods according to aspects of the present disclosure further include reacting the reaction mixtures under amplification conditions, producing at least first, second, and third amplification products when the target nucleic acid is present in the test sample, wherein detectable signals are generated by the fluorophores released from the hydrolysis probes.

Methods according to aspects of the present disclosure further include detecting the detectable signals of the released fluorophores.

Methods according to aspects of the present disclosure further include calculating a cycle threshold (Ct) value for the first fluorophore and the second fluorophore while reacting the first reaction mixture; calculating a Ct value for the third fluorophore and the fourth fluorophore while reacting the second reaction mixture; and calculating a Ct value for the fifth fluorophore and the sixth fluorophore while reacting the third reaction mixture.

Methods according to aspects of the present disclosure further include determining that the test sample contains the target nucleic acid when the Ct value for all of: 1) the first fluorophore and the second fluorophore of the first reaction mixture; 2) the third fluorophore and the fourth fluorophore of the second reaction mixture; and 3) the fifth fluorophore and the sixth fluorophore of the third reaction mixture; is positive and less than a predetermined value.

Figure 1B:
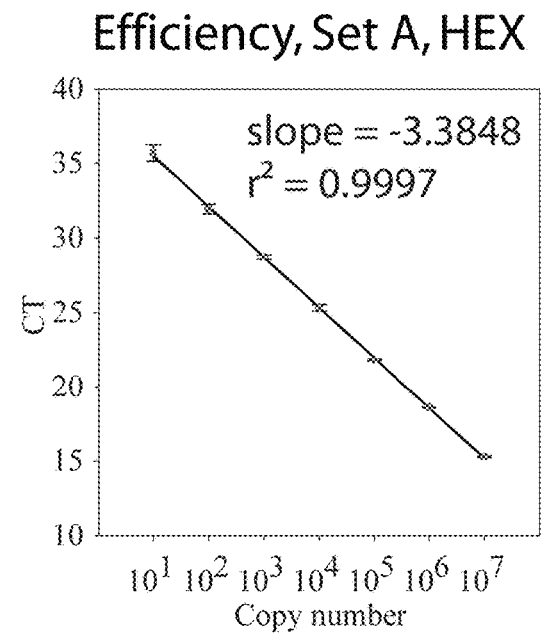
FIG. 1B is a graph showing efficiency amplification for ultra-specific and ultra-sensitive SARS-CoV-2 detection using Set A indicating an extremely high correlation from 10^7 to 10^1 SARS nucleocapsid RNA in HEX channel.
Figure 1C:
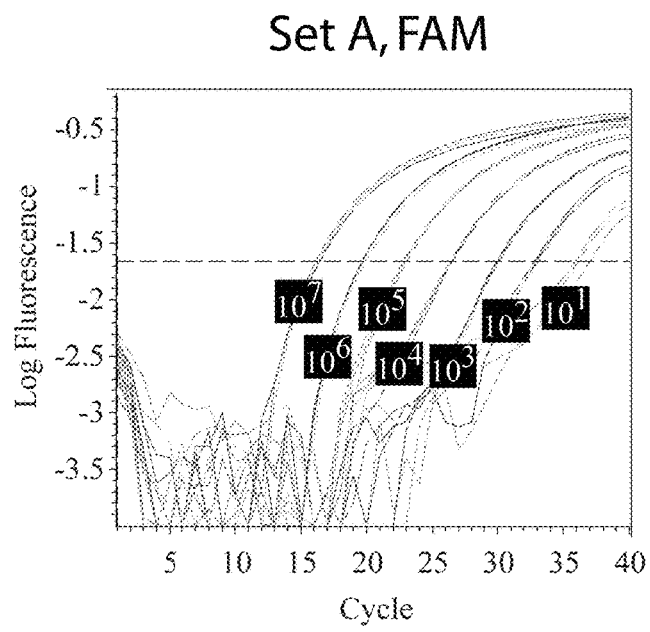
FIG. 1C is a graph showing representative traces demonstrating highly-reliable and high-precision SARS-CoV-2 detection using primers/probes Set A and indicating effective amplification and detection of 10^7 to 10^1 SARS-CoV-2 nucleocapsid RNA in FAM channel.
Figure 1D:
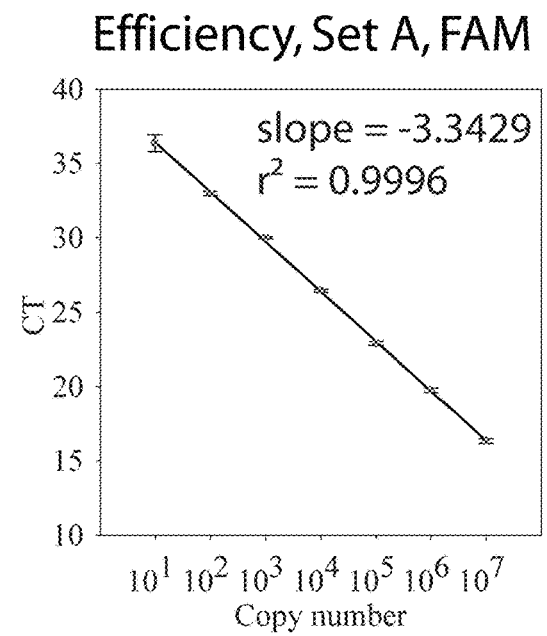
FIG. 1D is a graph showing efficiency amplification for ultra-specific and ultra-sensitive SARS-CoV-2 detection using Set A indicating an extremely high correlation from 10^7 to 10^1 SARS nucleocapsid RNA in FAM channel.
Figure 2A:
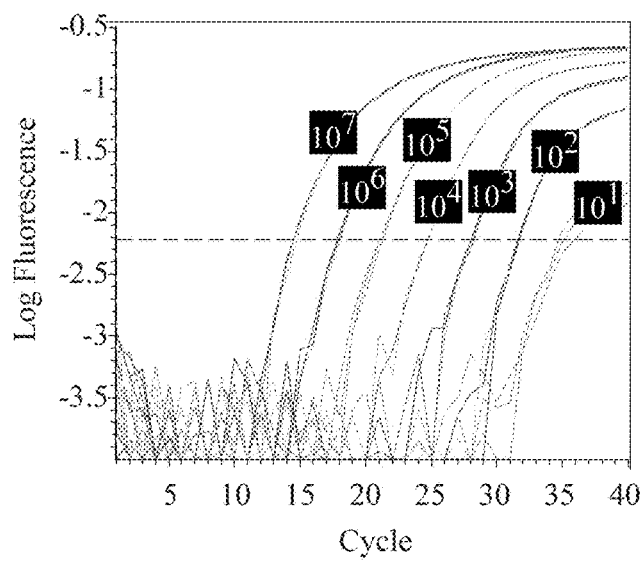
FIG. 2A is a graph showing representative traces demonstrating highly-reliable and high-precision SARS-CoV-2 detection using primers/probes Set B and indicating effective amplification and detection of 10^7 to 10^1 SARS-CoV-2 nucleocapsid RNA in HEX channel.
Figure 2B:
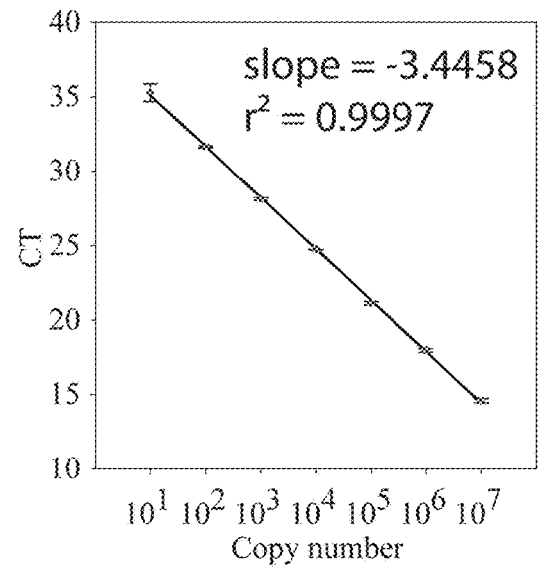
FIG. 2B is a graph showing efficiency amplification for ultra-specific and ultra-sensitive SARS-CoV-2 detection using Set B indicating an extremely high correlation from 10^7 to 10^1 SARS nucleocapsid RNA in HEX channel.
Figure 2C:
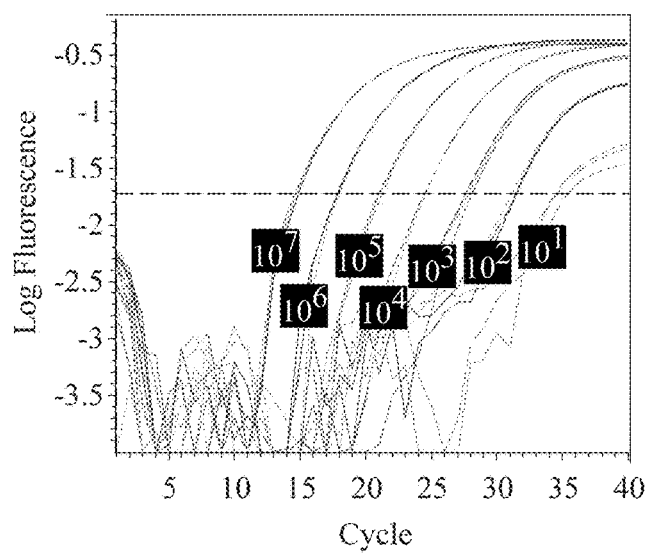
FIG. 2C is a graph showing representative traces demonstrating highly-reliable and high-precision SARS-CoV-2 detection using primers/probes Set B and indicating effective amplification and detection of 10^7 to 10^1 SARS-CoV-2 nucleocapsid RNA in FAM channel.
Figure 2D:
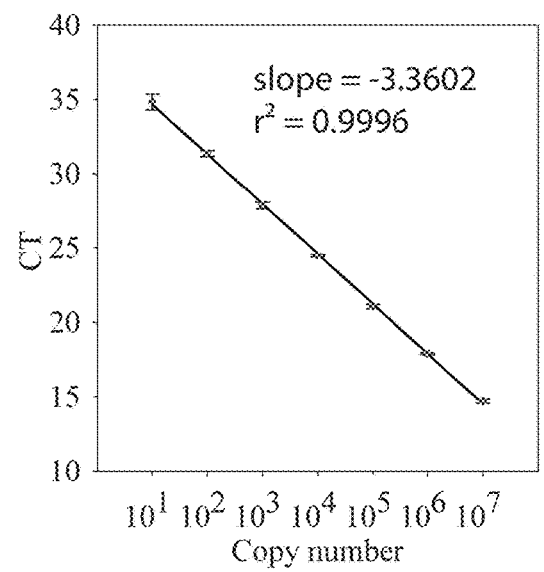
FIG. 2D is a graph showing efficiency amplification for Ultra-specific and Ultra-sensitive SARS-CoV-2 detection using Set B indicating an extremely high correlation from 10^7 to 10^1 SARS nucleocapsid RNA in FAM channel.
Figure 3A:
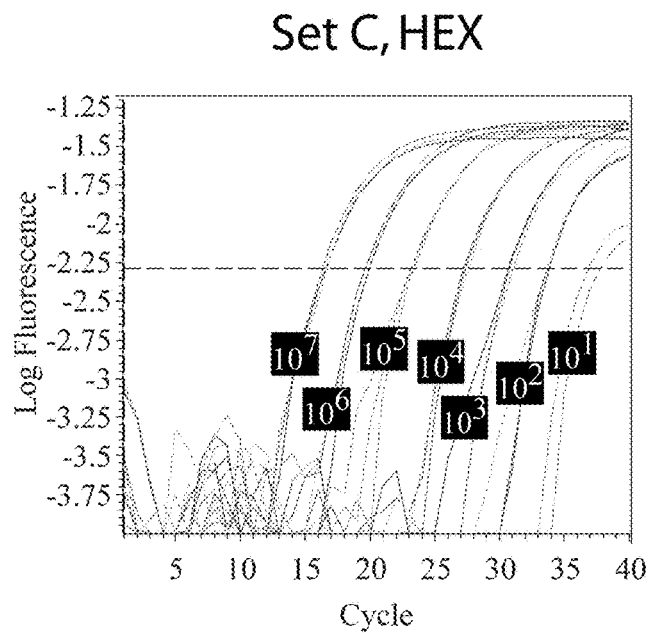
FIG. 3A is a graph showing representative traces demonstrating highly-reliable and high-precision SARS-CoV-2 detection using primers/probes Set C and indicating effective amplification and detection of 10^7 to 10^1 SARS-CoV-2 nucleocapsid RNA in HEX channel.
Figure 3B:
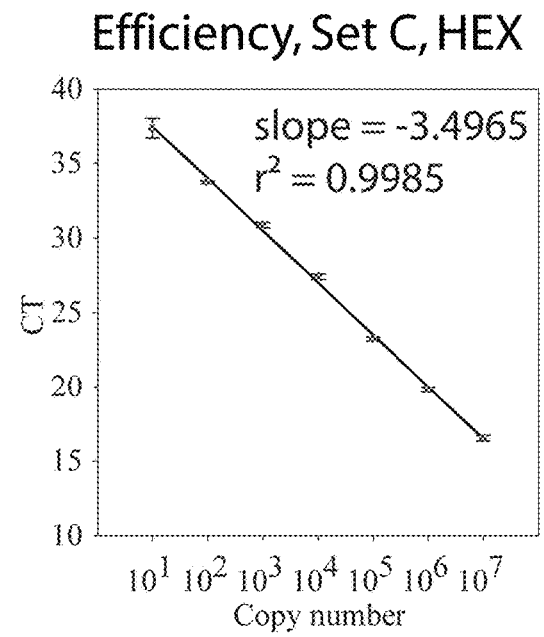
FIG. 3B is a graph showing efficiency amplification for ultra-specific and ultra-sensitive SARS-CoV-2 detection using Set C indicating an extremely high correlation from 10^7 to 10^1 SARS nucleocapsid RNA in HEX channel.
Figure 3C:
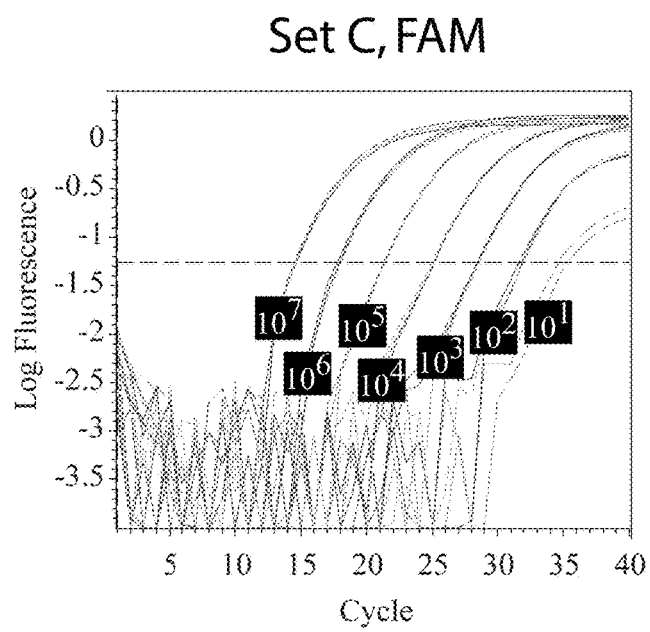
FIG. 3C is a graph showing representative traces demonstrating highly-reliable and high-precision SARS-CoV-2 detection using primers/probes Set C and indicating effective amplification and detection of 10^7 to 10^1 SARS-CoV-2 nucleocapsid RNA in FAM channe.
Figure 3D:
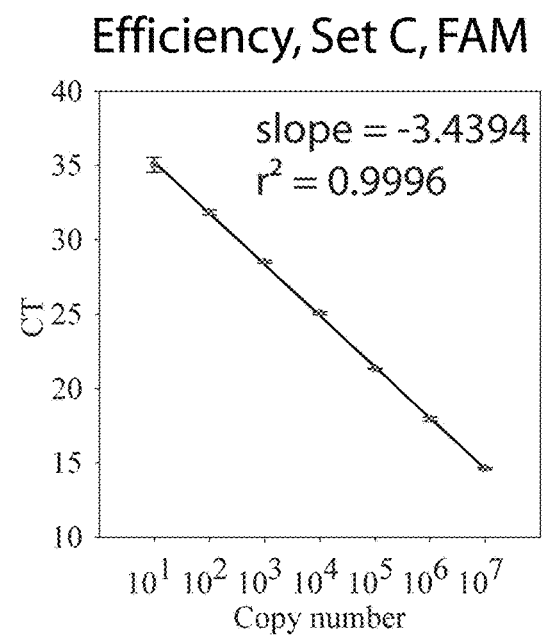
FIG. 3D is a graph showing efficiency amplification for ultra-specific and ultra-sensitive SARS-CoV-2 detection using Set C indicating an extremely high correlation from 10^7 to 10^1 SARS nucleocapsid RNA in FAM channel.
Figure 4A:
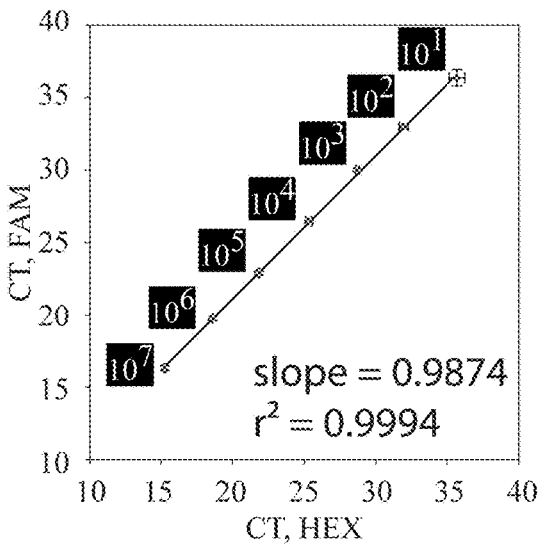
FIG. 4A is a graph indicating congruent ultra-specific and ultra-sensitive SARS-CoV-2 detection and amplification efficiency of Set A with a similar average delta CT change from 10^7 to 10^1 target RNA molecules. Note the impressive correlation reached by the used set.
Figure 4B:
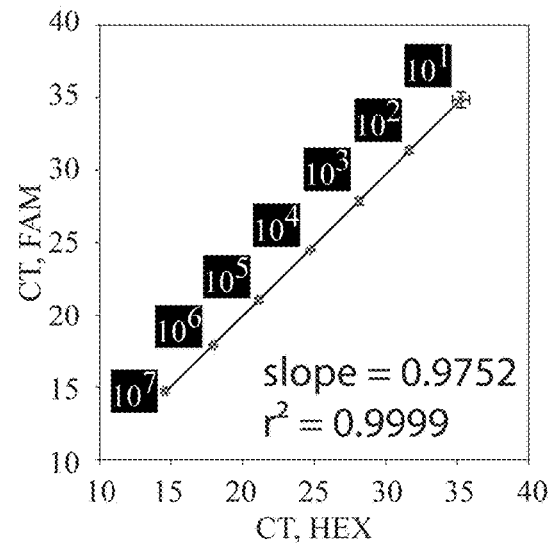
FIG. 4B is a graph indicating congruent ultra-specific and ultra-sensitive SARS-CoV-2 detection and amplification efficiency of Set B with a similar average delta CT change from 10^7 to 10^1 target RNA molecules. Note the impressive correlation reached by the used set.
Figure 4C:
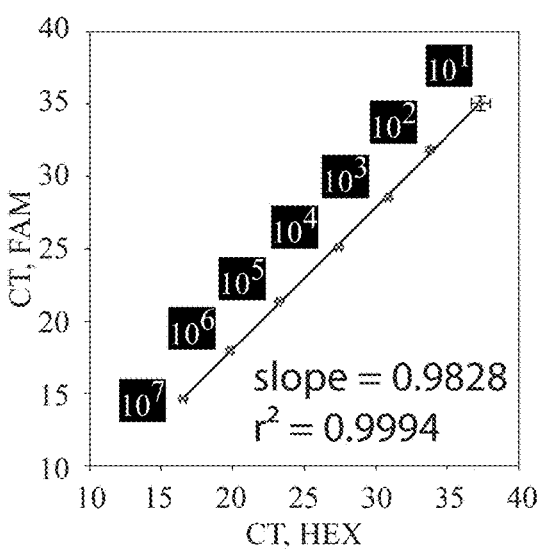
FIG. 4C is a graph indicating congruent ultra-specific and ultra-sensitive SARS-CoV-2 detection and amplification efficiency of Set C with a similar average delta CT change from 10^7 to 10^1 target RNA molecules. Note the impressive correlation reached by the used set.
Figure 4D:
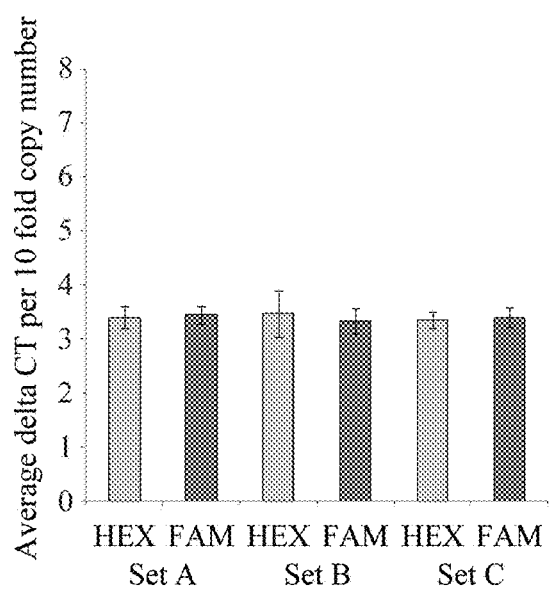
FIG. 4D is a graph indicating congruent ultra-specific and ultra-sensitive SARS-CoV-2 detection and amplification efficiency of Sets A, B and C with a similar average delta CT change across 10^7 to 10^1 target RNA molecules. Note the impressive, consistent average CT value obtained by the distinct channels used in each set.
Figure 5:
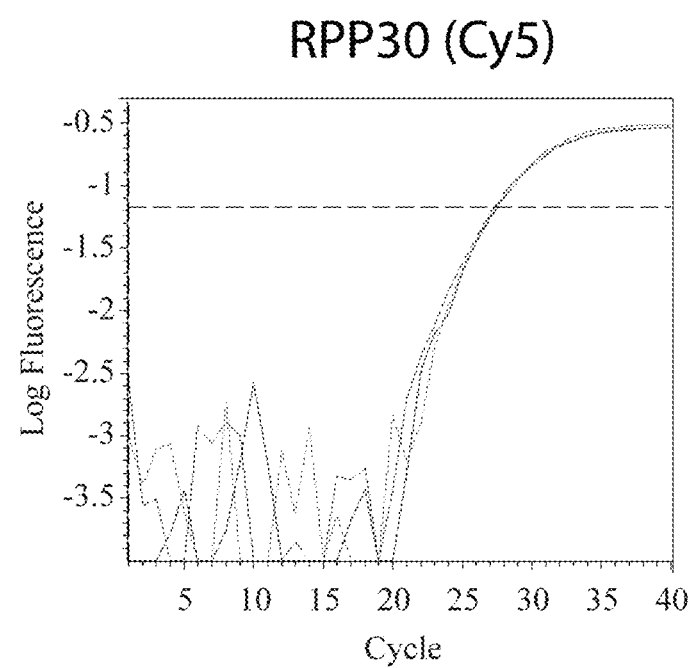
FIG. 5 is a graph showing representative traces for the RT-qPCR amplification reaction for the RPP30 endogenous control gene in Cy5 channel.
Figure 6A:
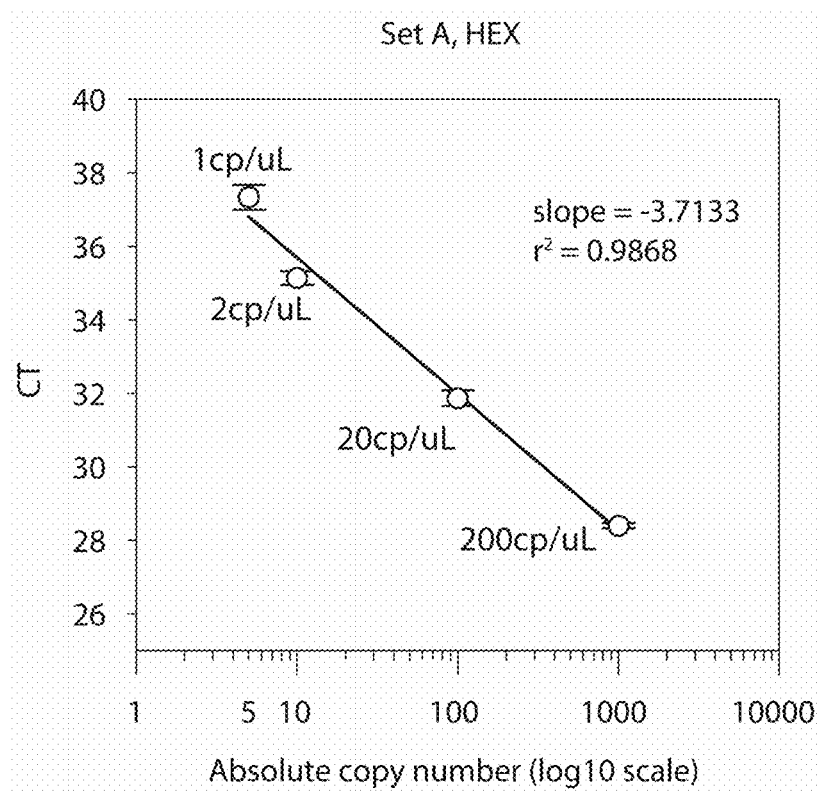
FIG. 6A is a graph demonstrating highly-reliable and high-precision SARS-CoV-2 detection using primers/probes Set A HEX channel, and indicating effective amplification and detection of 1 copy/uL, 2 copy/uL, 20 copy/uL and 200 copy/uL, corresponding to 5, 10, 100 and 1,000 absolute copies per reaction.
Figure 6B:
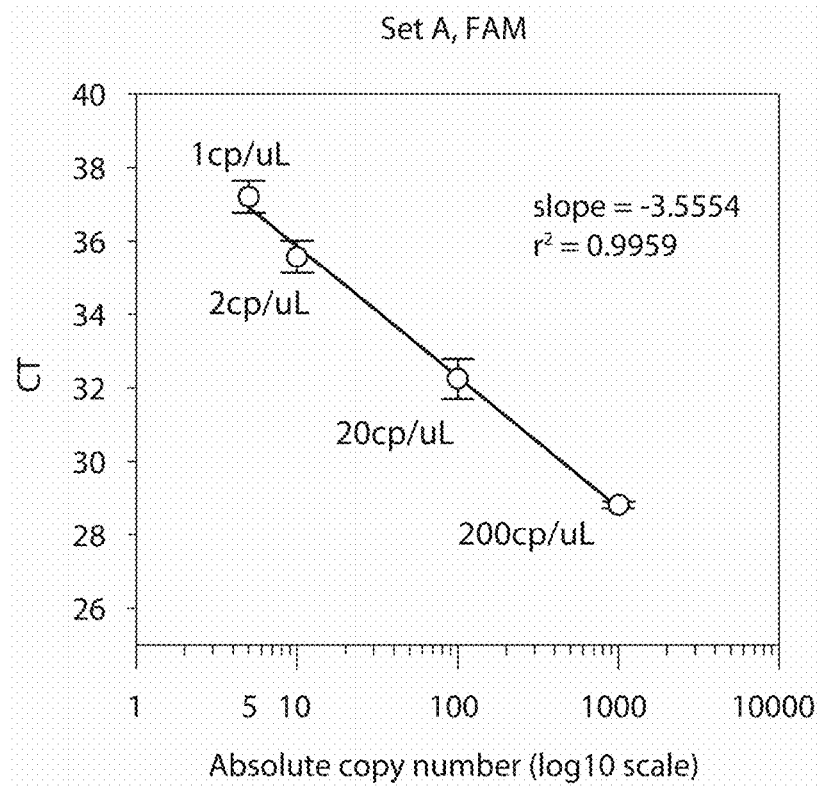
FIG. 6B is a graph demonstrating highly-reliable and high-precision SARS-CoV-2 detection using primers/probes Set A FAM channel, and indicating effective amplification and detection of 1 copy/uL, 2 copy/uL, 20 copy/uL and 200 copy/uL, corresponding to 5, 10, 100 and 1,000 absolute copies per reaction.
Figure 7A:
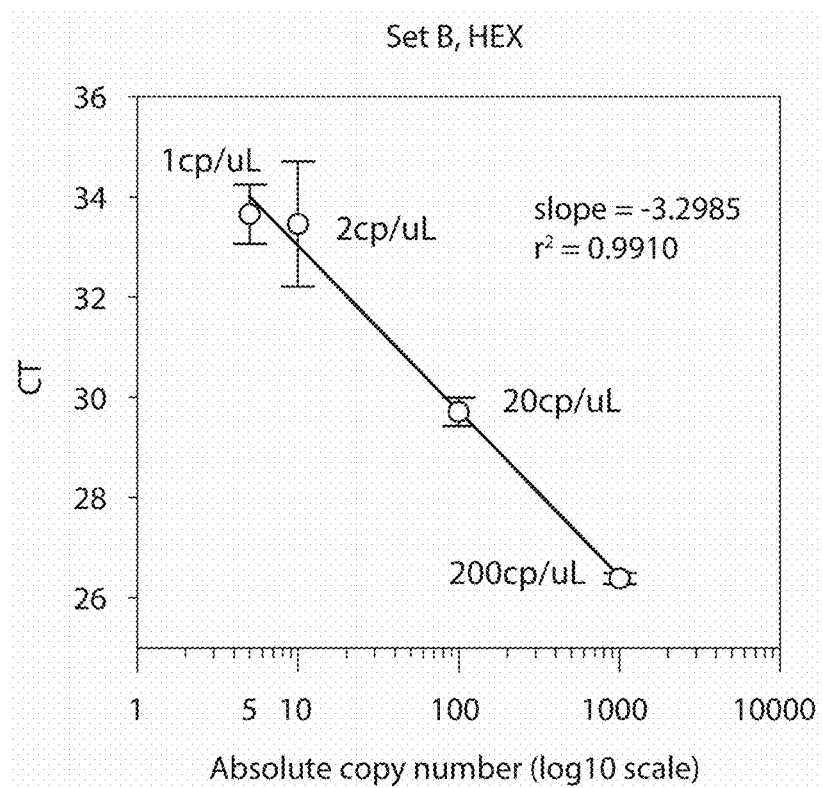
FIG. 7A is a graph demonstrating highly-reliable and high-precision SARS-CoV-2 detection using primers/probes Set B HEX channel, and indicating effective amplification and detection of 1 copy/uL, 2 copy/uL, 20 copy/uL and 200 copy/uL, corresponding to 5, 10, 100 and 1,000 absolute copies per reaction.
Figure 7B:
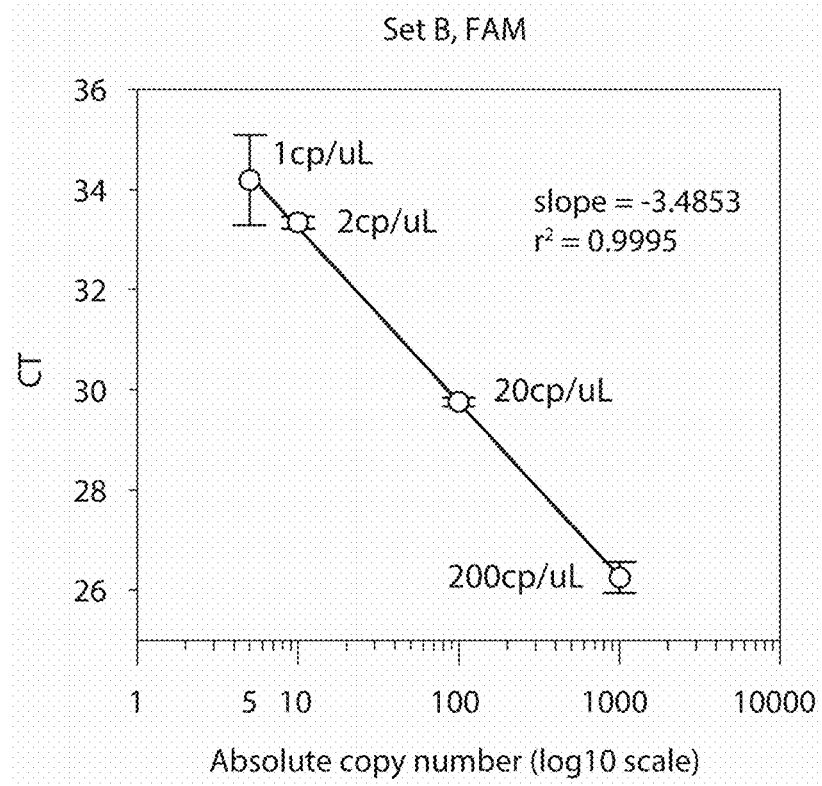
FIG. 7B is a graph demonstrating highly-reliable and high-precision SARS-CoV-2 detection using primers/probes Set B FAM channel, and indicating effective amplification and detection of 1 copy/uL, 2 copy/uL, 20 copy/uL and 200 copy/uL, corresponding to 5, 10, 100 and 1,000 absolute copies per reaction.
Figure 8A:
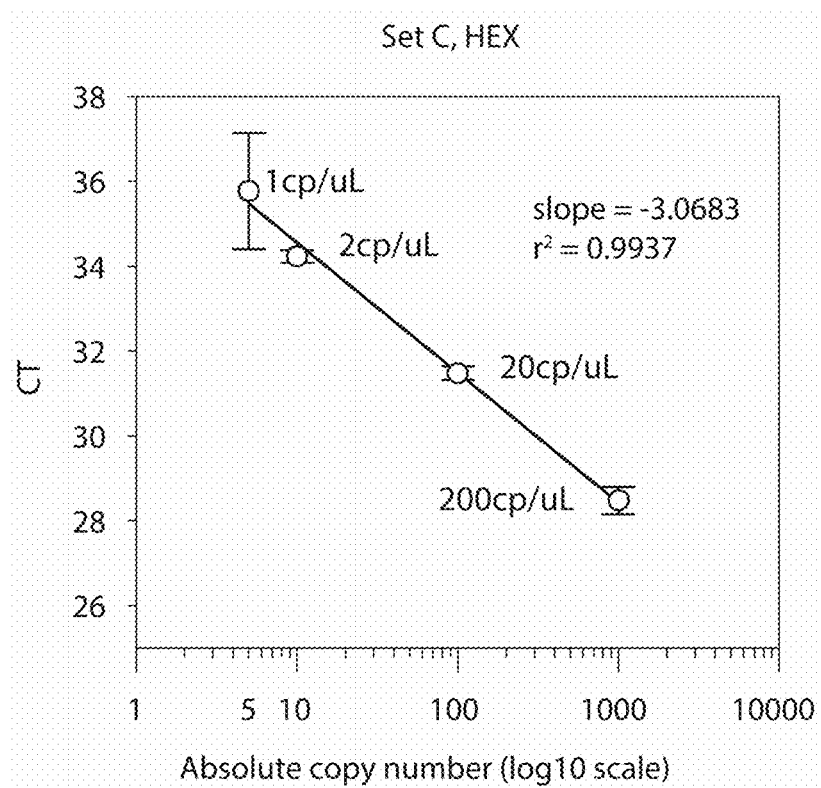
FIG. 8A is a graph demonstrating highly-reliable and high-precision SARS-CoV-2 detection using primers/probes Set C HEX channel, and indicating effective amplification and detection of 1 copy/uL, 2 copy/uL, 20 copy/uL and 200 copy/uL, corresponding to 5, 10, 100 and 1,000 absolute copies per reaction.
Figure 8B:
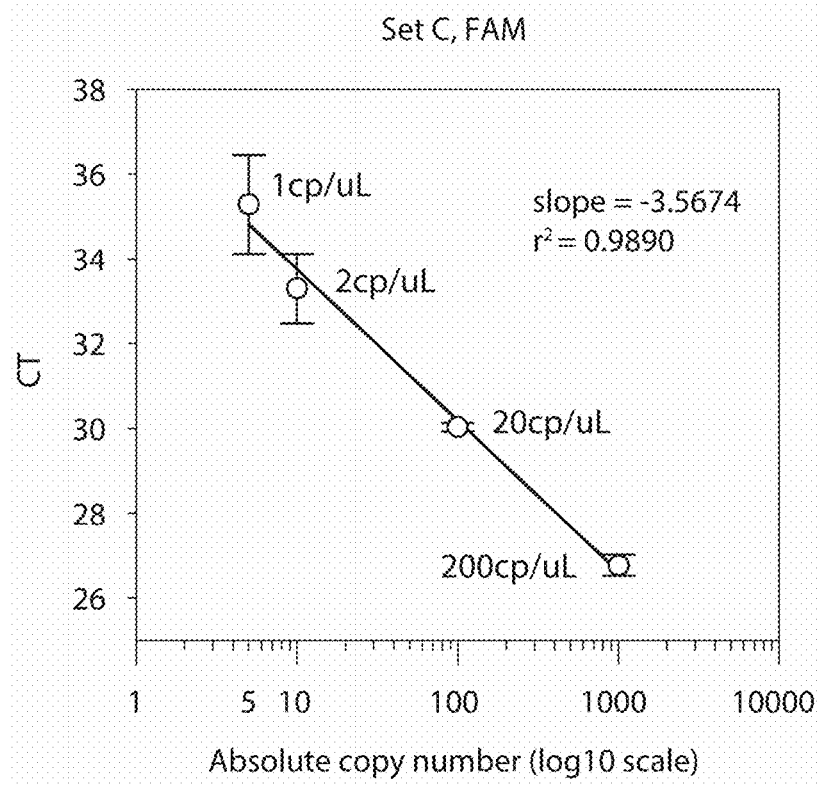
FIG. 8B is a graph demonstrating highly-reliable and high-precision SARS-CoV-2 detection using primers/probes Set C FAM channel, and indicating effective amplification and detection of 1 copy/uL, 2 copy/uL, 20 copy/uL and 200 copy/uL, corresponding to 5, 10, 100 and 1,000 absolute copies per reaction.
Figure 9:
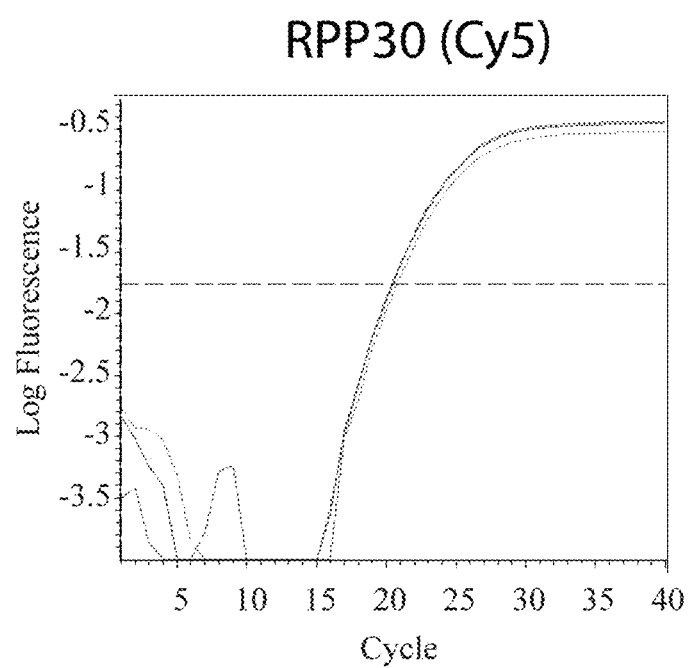
FIG. 9 is a graph showing representative traces for the RT-qPCR amplification reaction for the RPP30 endogenous control gene in the study with samples including 1-copy/uL of target RNA (FIGS. 6, 7, 8); RPP30 amplification was detected in Cy5 channel and using the second RPP30 alternative set.
Figure 10:
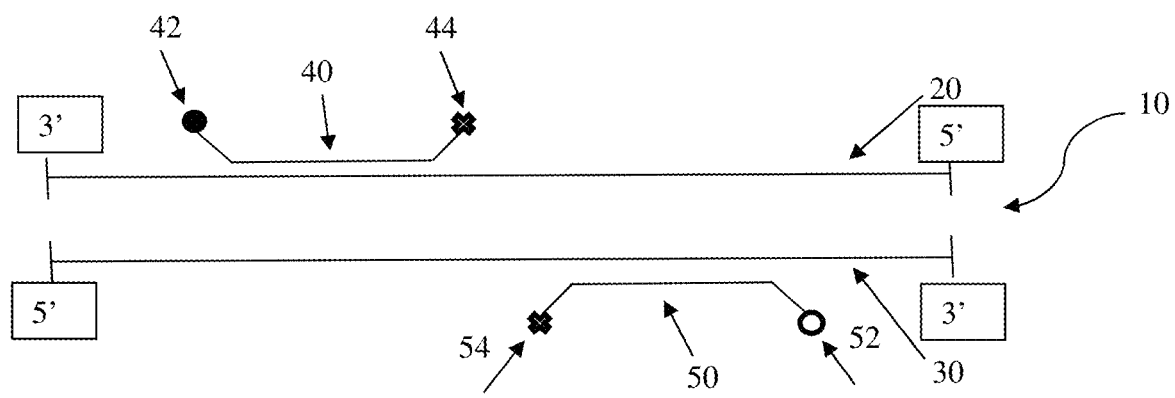
FIG. 10 is a schematic illustration of a double-stranded amplification product 10 of a first set of amplification primers using a target nucleic acid as template, the double-stranded amplification product 10 having a first strand 20 which is complementary to a second strand 30. Two hydrolysis probes are shown, a first hydrolysis probe 40 having a fluorophore 42 and a quencher 44, and a second hydrolysis probe 50, having a fluorophore 52 and a quencher 54, the hydrolysis probes 40 and 50 specific for highly-conserved segments of the target nucleic acid, and therefore also specific for the double-stranded amplification product 10.

Methods according to aspects of the disclosure include at least one, two, or three sets of amplification primers and hydrolysis probes with at least two separate corresponding readouts per set, wherein the amplification primers and hydrolysis probes are specific for highly-conserved segments of SARS-CoV-2 mRNA, do not recognize any human mRNA sequences or genes, and do not cross detect any RNA sequences from the other common, cold-causing coronaviruses 229E, NL63, OC43 or HUK1 (See FIGS. 1-9). Methods for SARS-CoV-2 according to aspects of the present disclosure detect as little as 1 copy/µL of SARS-CoV-2 virus per sample.

Methods according to aspects of the disclosure include at least three sets of amplification primers and hydrolysis probes with at least two separate corresponding readouts per set, wherein the amplification primers and hydrolysis probes are specific for highly-conserved segments of SARS-CoV-2 mRNA, do not recognize any human mRNA sequences or genes, and do not cross detect any RNA sequences from the other common, cold-causing coronaviruses 229E, NL63, OC43 or HUK1 (See FIGS. 1-9). Methods for SARS-CoV-2 according to aspects of the present disclosure detect as little as 1 copy/µL of SARS-CoV-2 virus per sample.

Methods of detecting intact severe acute respiratory syndrome coronavirus 2 (SARS-CoV-2) in a test sample including or suspected of including SARS-CoV-2, are provided according to aspects of the present disclosure which include: detecting the presence of a SARS-CoV-2 nucleic acid in the test sample by reverse-transcription quantitative polymerase chain reaction (RT-qPCR), wherein the RT-qPCR includes one, two, or three of i), ii), and iii):

i) forming a first reaction mixture including the test sample, nucleic acid amplification reagents, and a first set of amplification primers and hydrolysis probes, the first set including: a first hydrolysis probe, a second hydrolysis probe, and a first pair of amplification primers, wherein the first hydrolysis probe includes a first fluorophore and a quencher of the first fluorophore, and wherein the second hydrolysis probe includes a second fluorophore and a quencher of the second fluorophore, wherein the first pair of amplification primers and the first and second hydrolysis probes are specific for the SARS-CoV-2 nucleic acid, and wherein the first hydrolysis probe and the second hydrolysis probe are specific for an amplification product of the first pair of amplification primers;

ii) forming a second reaction mixture including the test sample, nucleic acid amplification reagents, and a second set of amplification primers and hydrolysis probes, the second set including: a third hydrolysis probe, a fourth hydrolysis probe, and a second pair of amplification primers, wherein the third hydrolysis probe includes a third fluorophore and a quencher of the third fluorophore, and wherein the fourth hydrolysis probe includes a fourth fluorophore and a quencher of the fourth fluorophore, wherein the second pair of amplification primers and the third and fourth hydrolysis probes are specific for the SARS-CoV-2 nucleic acid, and wherein the third hydrolysis probe and the fourth hydrolysis probe are specific for an amplification product of the second pair of amplification primers; and iii) forming a third reaction mixture including the test sample, nucleic acid amplification reagents, and a third set of amplification primers and hydrolysis probes, the third set including: a fifth hydrolysis probe, a sixth hydrolysis probe, and a third pair of amplification primers, wherein the fifth hydrolysis probe includes a fifth fluorophore and a quencher of the fifth fluorophore, wherein the sixth hydrolysis probe includes a sixth fluorophore and a quencher of the sixth fluorophore, and wherein the third pair of amplification primers and the fifth and sixth hydrolysis probes are specific for the SARS-CoV-2 nucleic acid, and wherein the fifth hydrolysis probe and the sixth hydrolysis probe are specific for an amplification product of the third pair of amplification primers.

The reaction mixtures may be separate or together, i.e. multiplexed.

Optionally, the reaction mixture, or reaction mixtures, contain a reverse transcriptase and the reaction mixtures are reacted under reverse transcription reaction conditions to produce SARS-CoV-2 cDNA from SARS-CoV-2 RNA in the test sample. Alternatively, the reverse transcription reaction is performed prior to generating the reaction mixtures, thereby generating SARS-CoV-2 cDNA from SARS-CoV-2 RNA in the test sample. The term "reverse transcription reaction conditions" refers to reaction conditions that promote annealing and/or extension of oligonucleotide sequences by a reverse transcription enzyme and include, but are not limited to, temperature, buffer type and amount, salt type and amount, ionic strength, pH, nucleotide type and amount, and polymerase type and amount.

In a further option, the RT-PCR includes digital PCR (dPCR). In a still further option, the dPCR is digital droplet PCR (ddPCR).

Such methods further include reacting the reaction mixtures under amplification conditions, producing first, second, and third amplification products when the SARS-CoV-2 nucleic acid is present in the test sample, wherein detectable signals are generated by the fluorophores released from the hydrolysis probes.

The term "amplification" refers to a method for copying a target nucleic acid, thereby producing amplified target nucleic acids which include copies of at least a portion of the target nucleic acid. Amplification methods included according to aspects of the present disclosure are those which include template directed primer extension catalyzed by a nucleic acid polymerase using a pair of primers which flank the target nucleic acid, illustratively including, but not limited to, Polymerase Chain Reaction (PCR), reverse-transcription PCR (RT-PCR). ligation-mediated PCR (LM-PCR), phi-29 PCR, and other nucleic acid amplification methods, for instance, as described in C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

The term "amplification conditions" refers to reaction conditions that promote annealing and/or extension of primer and probe oligonucleotide sequences and include, but are not limited to, temperature, buffer type and amount, salt type and amount, ionic strength, pH, temperature cycling, nucleotide type and amount, and polymerase type and amount.

The term "amplification product" refers to the product of an amplification. The size of an amplification product depends on the identity of the primers and target nucleic acid and can be selected to be a specified size, typically in the range of about 50 bp to 20000 bp.

The term "amplification primer" refers to an oligonucleotide that is capable of acting as a site of initiation of synthesis of a template directed primer extension product, i.e. amplification product, under amplification conditions. An oligonucleotide primer is typically about 10 to 30 contiguous nucleotides in length and may be longer or shorter, such as 15 to 30 contiguous nucleotides in length, and such as 18 to 30 contiguous nucleotides in length. An oligonucleotide primer is completely complementary, or substantially complementary, to a region of a template nucleic acid such that, under hybridization conditions, the oligonucleotide primer anneals to the complementary, or substantially complementary, region of the target nucleic acid.

Primer design for amplification of a target nucleic acid is well-known to those of skill in the art. Primers for amplification of a target nucleic acid are designed according to well-known methods and criteria. For instance, the annealing temperature of the primers should be about the same, within a few degrees, the primers should not form dimers with each other and the primers should not form secondary structures, such as hairpins. Methods and considerations for primer design and amplification procedures are described in detail in Yuryev, A., PCR Primer Design, Methods in Molecular Biology, vol. 42, Human Press, 2007; C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

Nucleotides, including, but not limited to, deoxynucleotide triphosphates (dNTPs) and analogs thereof are included in one or more of: an amplification reaction mixture, a primer, and/or a probe according to aspects of the present disclosure.

Optionally, one or more nucleotide analogs is included in one or more of: an amplification reaction mixture, a primer, and/or a probe according to aspects of the present disclosure. The term "nucleotide analog" in this context refers to a modified or non-naturally occurring nucleotide, particularly nucleotide analogs which can be polymerized, with naturally occurring nucleotides or non-naturally occurring nucleotides, by template directed nucleic acid amplification catalyzed by a nucleic acid polymerase. Nucleotide analogs are well-known in the art. Particular nucleotide analogs are capable of Watson-Crick pairing via hydrogen bonds with a complementary nucleotide and illustratively include, but are not limited to, those containing an analog of a nucleotide base such as substituted purines or pyrimidines, deazapurines, methylpurines, methylpyrimidines, aminopurines, aminopyrimidines, thiopurines, thiopyrimidines, indoles, pyrroles, 7-deazaguanine, 7-deazaadenine, 7-methylguanine, hypoxanthine, pseudocytosine, pseudoisocytosine, isocytosine, isoguanine, 2-thiopyrimidines, 4-thiothymine, 6-thioguanine, nitropyrrole, nitroindole, and 4-methylindole. Nucleotide analogs include those containing an analog of a deoxyribose such as a substituted deoxyribose, a substituted or non-substituted arabinose, a substituted or non-substituted xylose, and a substituted or non-substituted pyranose. Nucleotide analogs include those containing an analog of a phosphate ester such as phosphorothioates, phosphorodithioates, phosphoroamidates, phosphoroselenoates, phosophoroanilothioates, phosphoroanilidates, phosphoroamidates, boronophosphates, phosphotriesters, and alkylphosphonates such as methylphosphonates.

Optionally, one or more $T_m$ increasing nucleotide analogs is included in one or more of: an amplification reaction mixture, a primer, and/or a probe according to aspects of the present disclosure. $T_m$ increasing nucleotide analogs include, but are not limited to, locked nucleic acid nucleotides, peptide nucleic acid nucleotides, and bridged nucleic acid nucleotides.

The reaction mixtures may be separate or together, i.e. multiplexed.

Methods of detecting a target nucleic acid in a test sample including or suspected of including the target nucleic acid, are provided according to aspects of the present disclosure in a multiplex format wherein at least two or more of the reaction mixtures are present together, such as in a reaction vessel, and wherein a signal from each of the first fluorophore, second fluorophore, third fluorophore, fourth fluorophore, fifth fluorophore, and sixth fluorophore, when present together in the reaction mixture, are detectably different such as by detectably different emission maxima, or such as by different excitation maxima applied at different times.

Methods of detecting intact severe acute respiratory syndrome coronavirus 2 (SARS-CoV-2) in a test sample including or suspected of including SARS-CoV-2, are provided according to aspects of the present disclosure in a multiplex format wherein at least two or more of the reaction mixtures are present together, such as in a reaction vessel, and wherein each of the first fluorophore, second fluorophore, third fluorophore, fourth fluorophore, fifth fluorophore, and sixth fluorophore, when present together in the reaction mixture, are detectably different such as by detectably different emission maxima, or such as by different excitation maxima applied at different times.

Methods described can be performed in any suitable container, also called a reaction vessel herein. According to aspects of the present disclosure, for example, where multiple samples are to be assayed, a multi-chamber container can be used. Multi-chamber containers illustratively include, but are not limited to, multi-depression substrates such as slides, silicon chips, trays, droplets, and multi-well plates.

Methods of detecting a target nucleic acid in a test sample including, or suspected of including, the target nucleic acid, are provided according to aspects of the present disclosure which include: detecting the presence of a target nucleic acid in the test sample by quantitative polymerase chain reaction (qPCR), wherein the qPCR includes: forming a reaction mixture including the test sample, nucleic acid amplification reagents, and one, two, or more of i), ii), and iii) as follows:
  i) a first set of amplification primers and hydrolysis probes, the first set including: a first hydrolysis probe, a second hydrolysis probe, and a first pair of amplification primers, wherein the first hydrolysis probe includes a first fluorophore and a quencher of the first fluorophore, and wherein the second hydrolysis probe includes a second fluorophore and a quencher of the second fluorophore, wherein the first pair of amplification primers and the first and second hydrolysis probes are specific for the target nucleic acid, and wherein the first hydrolysis probe and the second hydrolysis probe are specific for an amplification product of the first pair of amplification primers;
  ii) a second set of amplification primers and hydrolysis probes, the second set including: a third hydrolysis probe, a fourth hydrolysis probe, and a second pair of amplification primers, wherein the third hydrolysis probe includes a third fluorophore and a quencher of the third fluorophore, and wherein the fourth hydrolysis probe includes a fourth fluorophore and a quencher of the fourth fluorophore, wherein the second pair of amplification primers and the third and fourth hydrolysis probes are specific for the target nucleic acid, and wherein the third hydrolysis probe and the fourth hydrolysis probe are specific for an amplification product of the second pair of amplification primers; and
  iii) a third set of amplification primers and hydrolysis probes, the third set including: a fifth hydrolysis probe, a sixth hydrolysis probe, and a third pair of amplification primers, wherein the fifth hydrolysis probe includes a fifth fluorophore and a quencher of the fifth fluorophore, and wherein the sixth hydrolysis probe includes a sixth fluorophore and a quencher of the sixth fluorophore, wherein the third pair of amplification primers and the fifth and sixth hydrolysis probes are specific for the target nucleic acid, and wherein the fifth hydrolysis probe and the sixth hydrolysis probe are specific for an amplification product of the third pair of amplification primers.

Methods of detecting intact severe acute respiratory syndrome coronavirus 2 (SARS-CoV-2) in a test sample including or suspected of including SARS-CoV-2, are provided according to aspects of the present disclosure which include: detecting the presence of a SARS-CoV-2 nucleic acid in the test sample by reverse-transcription quantitative polymerase chain reaction (RT-qPCR), wherein the RT-qPCR includes: forming a reaction mixture including the test sample, nucleic acid amplification reagents, and one, two, or more of i), ii), and iii) as follows:
  i) a first set of amplification primers and hydrolysis probes, the first set including: a first hydrolysis probe, a second hydrolysis probe, and a first pair of amplification primers, wherein the first hydrolysis probe includes a first fluorophore and a quencher of the first fluorophore, and wherein the second hydrolysis probe includes a second fluorophore and a quencher of the second fluorophore, wherein the first pair of amplification primers and the first and second hydrolysis probes are specific for the SARS-CoV-2 nucleic acid, and wherein the first hydrolysis probe and the second hydrolysis probe are specific for an amplification product of the first pair of amplification primers;

ii) a second set of amplification primers and hydrolysis probes, the second set including: a third hydrolysis probe, a fourth hydrolysis probe, and a second pair of amplification primers, wherein the third hydrolysis probe includes a third fluorophore and a quencher of the third fluorophore, wherein the fourth hydrolysis probe includes a fourth fluorophore and a quencher of the fourth fluorophore, wherein the second pair of amplification primers and the third and fourth hydrolysis probes are specific for the SARS-CoV-2 nucleic acid, and wherein the third hydrolysis probe and the fourth hydrolysis probe are specific for an amplification product of the second pair of amplification primers; and iii) a third set of amplification primers and hydrolysis probes, the third set including: a fifth hydrolysis probe, a sixth hydrolysis probe, and a third pair of amplification primers, wherein the fifth hydrolysis probe includes a fifth fluorophore and a quencher of the fifth fluorophore, and wherein the sixth hydrolysis probe includes a sixth fluorophore and a quencher of the sixth fluorophore, wherein the third pair of amplification primers and the fifth and sixth hydrolysis probes are specific for the SARS-CoV-2 nucleic acid, and wherein the fifth hydrolysis probe and the sixth hydrolysis probe are specific for an amplification product of the third pair of amplification primers.

Optionally, the reaction mixture, or reaction mixtures, contain a reverse transcriptase and the reaction mixtures are reacted under conditions to produce target cDNA from target RNA in the test sample. Alternatively, the reverse transcription reaction is performed prior to generating the reaction mixtures, thereby generating target cDNA from target RNA in the test sample.

In a further option, the qPCR and/or RT-PCR includes digital PCR (dPCR). In a still further option, the dPCR is digital droplet PCR (ddPCR).

Optionally, a positive control is included in the reaction mixture or reaction mixtures.

Such methods further include reacting the reaction mixtures under amplification conditions, producing corresponding amplification products when the target nucleic acid is present in the test sample, wherein detectable signals are generated by the fluorophores released from the hydrolysis probes indicative of presence of the amplification products.

The detectable signals of the released fluorophores of the hydrolysis probes indicative of the presence of the amplified products are detected and a cycle threshold (Ct) value is calculated for the detected signals of the fluorophores while reacting the reaction mixture. It is determined that the test sample contains the target nucleic acid when the Ct value for all of the fluorophores in the reaction mixture is positive and less than a predetermined value.

The term "Ct" refers to the number of amplification cycles, such as PCR cycles, required for the detectable signal of a released, i.e. not quenched by a quencher, fluorophore of a hydrolysis probe indicative of production of an amplification product, i.e. a positive result, exceeds a background level of fluorescence, i.e. crosses a threshold number of cycles to exceed the background level of fluorescence. According to aspects of the methods, the Ct value indicative of a positive result is less than 40. According to aspects of the methods, the Ct value indicative of a positive result is less than 30. According to aspects of the methods, the Ct value indicative of a positive result is less than 20. According to aspects of the methods, the Ct value indicative of a positive result is less than 40, 39, 38, 37, 36, 35, 34, 33, 32, or 31. According to aspects of the methods, the Ct value indicative of a positive result is less than 30, 29, 28, 27, 26, 25, 24, 23, 22, or 21. According to aspects of the methods, the Ct value indicative of a positive result is less than 20, 19, 18, 17, 16, 15, 14, 13, 12, or 11.

Methods of detecting intact severe acute respiratory syndrome coronavirus 2 (SARS-CoV-2) in a test sample including or suspected of including SARS-CoV-2, are provided according to aspects of the present disclosure which include: detecting the presence of a SARS-CoV-2 nucleic acid encoding nucleocapsid phosphoprotein in the test sample by reverse-transcription quantitative polymerase chain reaction (RT-qPCR), wherein the RT-qPCR includes one, two, or three of i), ii), and iii):

i) forming a first reaction mixture, the first reaction mixture including the test sample, nucleic acid amplification reagents, and a first set of amplification primers and hydrolysis probes, the first set including: a first hydrolysis probe including SEQ ID NO:3, a second hydrolysis probe including SEQ ID NO:4, and primers including SEQ ID NO:1 and SEQ ID NO:2, wherein the first hydrolysis probe includes a first fluorophore and a quencher of the first fluorophore, wherein the second hydrolysis probe includes a second fluorophore and a quencher of the second fluorophore, and wherein the first hydrolysis probe and the second hydrolysis probe are specific for an amplification product of the first pair of amplification primers;

ii) forming a second reaction mixture, the second reaction mixture including the test sample, nucleic acid amplification reagents, and a second set of amplification primers and hydrolysis probes, the second set including: a third hydrolysis probe including SEQ ID NO:7, a fourth hydrolysis probe including SEQ ID NO:8, and primers including SEQ ID NO:5 and SEQ ID NO:6, wherein the third hydrolysis probe includes a third fluorophore and a quencher of the third fluorophore, wherein the fourth hydrolysis probe includes a fourth fluorophore and a quencher of the fourth fluorophore, and wherein the third hydrolysis probe and the fourth hydrolysis probe are specific for an amplification product of the second pair of amplification primers; and iii) a forming a third reaction mixture, the third reaction mixture including the test sample, nucleic acid amplification reagents, and a third set of amplification primers and hydrolysis probes, the third set including: a fifth hydrolysis probe including SEQ ID NO:11, a sixth hydrolysis probe including SEQ ID NO:12, and primers including SEQ ID NO:9 and SEQ ID NO:10, wherein the fifth hydrolysis probe includes a fifth fluorophore and a quencher of the fifth fluorophore, wherein the sixth hydrolysis probe includes a sixth fluorophore and a quencher of the sixth fluorophore, and wherein the fifth hydrolysis probe and the sixth hydrolysis probe are specific for an amplification product of the third pair of amplification primers.

The reaction mixtures may be separate or together, i.e. multiplexed.

Optionally, the reaction mixture, or reaction mixtures, contain a reverse transcriptase and the reaction mixtures are reacted under conditions to produce target cDNA from target RNA in the test sample. Alternatively, the reverse transcription reaction is performed prior to generating the reaction mixtures, thereby generating target cDNA from target RNA in the test sample.

In a further option, the RT-PCR includes digital PCR (dPCR). In a still further option, the dPCR is digital droplet PCR (ddPCR).

Such methods further include reacting the reaction mixtures under amplification conditions, producing first, second, and third amplification products when the SARS-CoV-2 nucleic acid encoding nucleocapsid phosphoprotein is present in the test sample, wherein detectable signals are generated by the first, second, third, fourth, fifth, and sixth fluorophores released from the hydrolysis probes.

Such methods further include detecting the detectable signals of the first, second, and third amplification products; calculating a cycle threshold (Ct) value for the first fluorophore and the second fluorophore while reacting the first reaction mixture; calculating a Ct value for the third fluorophore and the fourth fluorophore while reacting the second reaction mixture; calculating a Ct value for the fifth fluorophore and the sixth fluorophore while reacting the third reaction mixture; and determining that the test sample contains SARS-CoV-2 when the Ct value for all of: 1) the first fluorophore and the second fluorophore of the first reaction mixture; 2) the third fluorophore and the fourth fluorophore of the second reaction mixture; and 3) the fifth fluorophore and the sixth fluorophore of the third reaction mixture; is positive and less than a predetermined value.

According to aspects of the present disclosure, the first fluorophore is FAM or HEX, the second fluorophore is FAM or HEX but not identical to the first fluorophore, the quencher of the first fluorophore is Black Hole Quencher 1 (BHQ1), and the quencher of the second fluorophore is BHQ1; the third fluorophore is FAM or HEX, the fourth fluorophore is FAM or HEX but not identical to the third fluorophore, the quencher of the third fluorophore is BHQ1, and the quencher of the fourth fluorophore is BHQ1; and the fifth fluorophore is FAM or HEX, the sixth fluorophore is FAM or HEX but not identical to the fifth fluorophore, the quencher of the fifth fluorophore is BHQ1, and the quencher of the sixth fluorophore is BHQ1.

The test sample can be any biological or environmental sample that includes, or may include, nucleic acids.

According to aspects of the present disclosure, the test sample is, or is derived from, a biological sample obtained from a mammalian subject. A biological sample obtained from a subject can be, but is not limited to, a sample of saliva, blood, plasma, serum, mucous, urine, feces, nasal material, cerebrospinal fluid, cerebroventricular fluid, pleural fluids, pulmonary and bronchial lavage samples, sweat, tears, semen, bladder wash samples, amniotic fluid, lymph, hair, skin, tumor, and peritoneal fluid.

A mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. Subjects can be either gender and can be any age. In aspects of methods of the present disclosure, the subject is human.

According to aspects of the present disclosure, the test sample is, or is derived from, an environmental sample. An environmental sample can be, but is not limited to, a liquid, gas, or solid sample, including, but not limited to, a water sample, a sewage sample, an air sample, a surface swab, a food sample, a beverage sample, a clothing sample, and a soil sample. According to aspects of the present disclosure, the test sample is a sewage sample.

Optionally, the test sample is or includes purified nucleic acids according to methods of detecting a target nucleic acid in a test sample according to aspects of the present disclosure.

The term "purified nucleic acids" as used herein refers to nucleic acids that are removed from their natural environment. Purified nucleic acids may be at least 50% free from other components with which they are naturally associated, such as 50%, 60%, 75%, 85%, 95%, 99%, or more, free from other components with which they are naturally associated.

Optionally, the test sample is or includes purified DNA or RNA according to methods of detecting a target nucleic acid in a test sample according to aspects of the present disclosure.

The term "purified DNA" as used herein refers to DNA that is removed from its natural environment. Purified DNA may be at least 50% free from other components with which it is naturally associated, such as 50%, 60%, 75%, 85%, 95%, 99%, or more, free from other components with which it is naturally associated.

The term "purified RNA" as used herein refers to RNA that is removed from its natural environment. Purified RNA may be at least 50% free from other components with which it is naturally associated, such as 50%, 60%, 75%, 85%, 95%, 99%, or more, free from other components with which it is naturally associated. According to particular aspects, purified RNA is at least 50% free of DNA, such as 50%, 60%, 75%, 85%, 95%, 99%, or more, free of DNA.

The target nucleic acid can be any nucleic acid whose presence is to be detected according to aspects of the present disclosure and can be any nucleic acid, such as DNA or RNA. The target nucleic acid can be a nucleic acid present in, or putatively present in, a test sample obtained from, or derived from, a biological sample, an environmental sample or any source, a vertebrate or invertebrate organism, or cell, including but not limited to, a virus, a bacterium, a fungus, a mycoplasma, a plant, a mammal, a bird, an amphibian, insect, or a reptile. A target nucleic acid can be a nucleic acid present in, or putatively present in, a test sample obtained from, or derived from, a putatively abnormal cell, such as a cancer cell, such as from a biopsy of a subject.

A hydrolysis probe is a single stranded oligonucleotide which specifically hybridizes to a target sequence in a test sample under amplification conditions in a reaction mixture. An oligonucleotide hydrolysis probe is completely complementary, or substantially complementary, to a region of a template nucleic acid such that, under hybridization conditions, the oligonucleotide hydrolysis probe anneals to the complementary region of the target nucleic acid. Hydrolysis probes are labeled with a fluorophore, a FRET donor, at or near the 5' end of the probe and also include a fluorescence quencher, a FRET acceptor, at or near the 3' end of the probe. The length of the hydrolysis probe is selected such that the fluorophore and corresponding fluorescence quencher interact to cause quenching of the fluorophore when the hydrolysis probe is intact. The 5'→3' exonuclease activity of a polymerase present during the amplification reaction cleaves a 5' portion of the hydrolysis probe, thereby releasing the fluorophore at or near the 5' end of the hydrolysis probe, resulting in the fluorophores no longer being sufficiently adjacent for the fluorescence quencher to inhibit fluorescence emission by the FRET donor fluorophore, further resulting in a fluorescent signal emitted by the FRET donor fluorophore. Typically, a hydrolysis probe has a length in the range of 15 to 35 contiguous nucleotides in length, such as 16 to 30 contiguous nucleotides in length, such as 18 to 25 contiguous nucleotides in length, and may be shorter or longer.

According to aspects of the present disclosure, the at least two hydrolysis probes and associated pair of primers are directed to opposite strands of an amplification product. According to aspects of the present disclosure, one of the two hydrolysis probes is directed to a first strand of the amplification product and therefore has a sequence complementary to the first strand of the amplification product and the second of the two hydrolysis probes is directed to the second strand of the amplification product and therefore has a sequence complementary to the second strand of the amplification product.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

A "substantially complementary" nucleic acid sequence has at least 85% complementarity to a target sequence, or at least 86%, 87%, 88%, 89%, 90%, 91%, 92%, 93%, 94%, 95%, 96%, 97%, 98%, 99%, or greater, complementarity to a target nucleic acid sequence.

The phrase "specific for" in reference to a target nucleic acid, such as but not limited to a SARS-CoV-2 nucleic acid, refers to a property of a primer or probe to specifically hybridize to a target nucleic acid without substantial hybridization to nucleic acids other than the target nucleic acid in a sample.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA-5' is 100% complementary to a region of the nucleotide sequence 5'-TTAGCTGG-3'.

Digital PCR (dPCR) can be used according to aspects of the present disclosure. dPCR is a type of quantitative PCR (qPCR) in which a PCR reaction mixture is separated into multiple partitioned compartments, such as reaction vessels, or water-in-oil emulsion droplets (e.g. for "droplet digital PCR" (ddPCR), such that either 1 or 0 target nucleic acid molecules is present in each individual partitioned compartment. Following PCR amplification, the number of positive vs negative reactions is determined and the quantification is derived from this result statistically, preferably using Poisson statistics.

dPCR, such as ddPCR, can include dividing a reaction mixture into a plurality of droplets useful as partitioned compartments, such as droplets produced by a water-in-oil emulsion technique.

The number of partitioned compartments in a dPCR method, such as a ddPCR method, according to aspects of the present disclosure is any appropriate number of partitioned compartments useful to provide a desired result. The number of partitioned compartments in a dPCR method, such as a ddPCR method, according to aspects of the present disclosure is in the range of about 1000 to about 50000 partitioned compartments, about 2000 to about 45000 partitioned compartments, about 3000 to about 40000 partitioned compartments, about 4000 to about 35000 partitioned compartments, about 5000 to about 30000 partitioned compartments, about 10000 to about 25000 partitioned compartments, or about 15000 to about 20000 partitioned compartments.

The number of partitioned compartments in a dPCR method, such as a ddPCR method, according to aspects of the present disclosure is any appropriate number of partitioned compartments useful to provide a desired result. The number of droplets used as partitioned compartments in a dPCR method, such as a ddPCR method, according to aspects of the present disclosure is in the range of about 1000 to about 50000 droplets, about 2000 to about 45000 droplets, about 3000 to about 40000 droplets, about 4000 to about 35000 droplets, about 5000 to about 30000 droplets, about 10000 to about 25000 droplets, or about 15000 to about 20000 droplets.

Each partitioned compartment, such as a reaction vessel, or water-in-oil emulsion droplet, can contain an appropriate volume for the PCR reaction mixture to be contained therein. According to aspects of the present disclosure, each partitioned compartment, such as a reaction vessel, or water-in-oil emulsion droplet, contains a nanoscale volume, i.e. about 1 nanoliter to about 999 nanoliters, microscale volume, i.e. about 1 microliter to about 999 microliters, or milliscale volume, i.e. about one milliliter to about 2 milliliters, although more, or less, may be used. According to aspects of the present disclosure, each droplet, contains a nanoscale volume, i.e. about 1 nanoliter to about 999 nanoliters, about 1 nanoliter to about 500 nanoliters, about 1 nanoliter to about 200 nanoliters, about 1 nanoliter to about 100 nanoliters, or more, or less.

Droplets can be generated using any appropriate method. According to aspects, droplets are generated using a water-in-oil emulsion technique. According to aspects, droplets can be generated using a commercially available droplet generator, such as for example, Bio-Rad QX200 Droplet Generator.

According to aspects of the present disclosure, detection of fluorescence for dPCR, such as ddPCR, is accomplished, for example, using a droplet reader such as a commercially available QX200 Droplet Digital Droplet Reader (Bio-Rad, USA).

Optionally, two or more reaction mixtures are included in single partitioned compartment, i.e. multiplexed, such as a reaction vessel, or a droplet, for example using distinguishable fluorophores.

Any of various fluorophores can be used to label the hydrolysis probes such that a detectable signal is obtained when the probes are degraded such that the fluorophore signal is no longer quenched by the quencher. For example, each of the first fluorophore, second fluorophore, third fluorophore, fourth fluorophore, fifth fluorophore, and sixth fluorophore, when included in the same reaction mixture, are detectably different due to differences such as different emission maxima when the probes are degraded such that the fluorophore signal is no longer quenched by the quencher. In a further example, the first, second, and third reaction mixtures are separate and the fluorophores in each reaction mixture are characterized by emission maxima that are detectably different from each other but each reaction mixture may include the same fluorophores as another, separate, reaction mixture.

Fluorophores useful in methods according to aspects of the present disclosure are FRET donors such as, but not limited to, 4-acetamido-4'-isothiocyanatostilbene-2,2'-disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcouluarin (Coumaran 151); Cy5, Cy7, cyanosine; DAPDXYL sulfonyl chloride; 4',6-diaminidino-2-phenylindole (DAPI); 5',5"'-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylaminolnaphthalene-1-sulfonyl chloride (DNS, dansyl chloride); 4-dimethylaminophenylazophenyl-4'-isothiocyanate (DAB ITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), 5-(4,6-dichlorotriazin-2-yl)aminofluorescein (DTAF), 2',7'-dimethoxy-4',5'-dichloro-6-carboxyfluorescein (JOE), hexachlorofluorescein (HEX), tetramethyl fluorescein (TET), and fluorescein isothiocyanate (FITC); fluorescamine; IAEDANS (5-({2-[(iodoacetyl)amino]ethyl}amino)naphthalene-1-sulfonic acid), Malachite Green isothiocyanate; 4-methylumbelliferone; NED, orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); tetramethyl rhodamine; N,N,N',N-tetramethyl-carboxyrhodamine (TAMRA); tetramethyl rhodamine isothiocyanate (TRITC); TEX 615, VIC, and Yakima Yellow.

According to aspects of the present disclosure, the fluorophore is a fluorescent polymeric dye, such as, but not limited to, brilliant violet fluorophores, see for example Chattopadhyay et al., Brilliant violet fluorophores: A new class of ultrabright fluorescent compounds for immunofluorescence experiments, Cytometry Part A, 81A(6):456-466, 2012.

Quenchers useful in methods according to aspects of the present disclosure are FRET acceptors such as, but not limited to, BHQ1, BHQ2, BHQ3, tetramethylrhodamine, N,N,N',N-tetramethyl-carboxyrhodamine (TAMRA); fluorescein, 4-(4'-dimethylaminophenylazo)benzoic acid (DABCYL), BODIPY FL, QSY 7, QSY 9, and Alexa647.

Typically, a FRET donor is attached to the hydrolysis probe and is present at or near the 5' end of a hydrolysis probe and a FRET acceptor is attached to the hydrolysis probe and is present at or near the 3' end of a hydrolysis probe, separated by a distance of about 20 to 30 nucleotides, although a greater or lesser distance is possible as long as the quenching activity of the quencher is capable of functioning at the selected distance.

Optionally, an internal quencher can be used to supplement the activity of a FRET pair including a FRET donor present at or near the 5' end of a hydrolysis probe and a FRET acceptor present at or near the 3' end of a hydrolysis probe. An internal quencher is attached to the hydrolysis probe between the FRET donor present at or near the 5' end of a hydrolysis probe and a FRET acceptor is present at or near the 3' end of a hydrolysis probe. An internal quencher can provide greater overall quenching of the FRET donor, lower background, and increase signal detection. Internal quenchers include, but are not limited to, the ZEN internal quencher and the TAO internal quencher.

Examples of FRET donor/acceptor pairs are described in Lakowicz, J. R., Principles of Fluorescence Spectroscopy, Springer, 3rd ed., 2006; and Haughland, R. P., The Handbook, A Guide to Fluorescent Probes and Labeling Technologies, 10th Ed., 2005.

One of skill in the art can easily determine which of various fluorophores and quenchers are to be used as FRET donor/acceptor pairs in a particular application.

Fluorophores are selected for inclusion in hydrolysis probes based on characteristics including, but not limited to, excitation maximum wavelength and emission maximum wavelength.

According to aspects of the present disclosure, at least two fluorophores are selected such that their emission maxima are detectably different, allowing for detection of fluorescence from the at least two fluorophores, thereby providing a separate signal from the at least two individual fluorophores when the at least two fluorophores are excited simultaneously, or at different times present in a single reaction mixture, or in separate reaction mixtures.

According to aspects of the present disclosure, two, three, four, five, six, seven, or more, fluorophores are selected such that their emission maxima are detectably different, allowing for simultaneous detection of fluorescence from the fluorophores, thereby providing a separate signal from the individual fluorophores when the fluorophores are excited simultaneously, or at different times, present in a single reaction mixture, or in separate reaction mixtures.

According to aspects of the present disclosure, at least two fluorophores are selected such that their emission maxima are not detectably different, allowing for detection of fluorescence from the at least two fluorophores, thereby providing combined signals from the at least two individual fluorophores when the at least two fluorophores are excited simultaneously, or at different times, present in a single reaction mixture, or in separate reaction mixtures.

According to aspects of the present disclosure, at least two fluorophores are selected such that their emission maxima are not detectably different, allowing for detection of fluorescence from the at least two fluorophores, thereby providing individual signals from the at least two individual fluorophores when the at least two fluorophores are excited simultaneously, or at different times, present in separate reaction mixtures.

According to aspects of the present disclosure, at least two fluorophores are selected such that their excitation maxima are detectably different and their emission maxima are either detectably different or not detectably different, allowing for detection of fluorescence from the at least two fluorophores, thereby providing a separate signal from the at least two individual fluorophores when the at least two fluorophores are excited simultaneously, or at different times present in a single reaction mixture, or in separate reaction mixtures.

According to aspects of the present disclosure, at least two fluorophores are selected such that their excitation maxima are not detectably different and their emission maxima are detectably different, allowing for detection of fluorescence from the at least two fluorophores, thereby providing a separate signal from the at least two individual fluorophores when the at least two fluorophores are excited simultaneously, or at different times present in a single reaction mixture, or in separate reaction mixtures.

According to aspects of the present disclosure, at least two fluorophores are selected such that their excitation maxima are not detectably different and their emission maxima are not detectably different, allowing for detection of fluorescence from the at least two fluorophores, thereby providing combined signals from the at least two individual fluorophores when the at least two fluorophores are excited simultaneously, or at different times, present in a single reaction mixture, or in separate reaction mixtures.

According to aspects of the present disclosure, the first fluorophore and the second fluorophore have distinguishable emission maxima, the third fluorophore and the fourth fluorophore have distinguishable emission maxima, and the fifth fluorophore and the sixth fluorophore have distinguishable emission maxima. Optionally, a seventh fluorophore included in a control hydrolysis probe has an emission maximum distinguishable from the first fluorophore and the second fluorophore. Optionally, a seventh fluorophore included in a control hydrolysis probe has an emission maximum distinguishable from the third fluorophore and the fourth fluorophore. Optionally, a seventh fluorophore included in a control hydrolysis probe has an emission maximum distinguishable from the fifth fluorophore and the sixth fluorophore.

According to aspects of the present disclosure, each of the first fluorophore, second fluorophore, third fluorophore, fourth fluorophore, fifth fluorophore, and sixth fluorophore have detectably different emission maxima. Optionally, a seventh fluorophore included in a control hydrolysis probe has an emission maximum distinguishable from each of the first fluorophore, second fluorophore, third fluorophore, fourth fluorophore, fifth fluorophore, and sixth fluorophore.

According to aspects of the present disclosure, the first fluorophore and the second fluorophore have distinguishable excitation maxima, the third fluorophore and the fourth fluorophore have distinguishable excitation maxima, and the fifth fluorophore and the sixth fluorophore have distinguishable excitation maxima. Optionally, a seventh fluorophore included in a control hydrolysis probe has an excitation maximum distinguishable from the first fluorophore and the second fluorophore. Optionally, a seventh fluorophore included in a control hydrolysis probe has an excitation maximum distinguishable from the third fluorophore and the fourth fluorophore. Optionally, a seventh fluorophore included in a control hydrolysis probe has an excitation maximum distinguishable from the fifth fluorophore and the sixth fluorophore.

According to aspects of the present disclosure, each of the first fluorophore, second fluorophore, third fluorophore, fourth fluorophore, fifth fluorophore, and sixth fluorophore have detectably different excitation maxima. Optionally, a seventh fluorophore included in a control hydrolysis probe has an excitation maximum distinguishable from each of the first fluorophore, second fluorophore, third fluorophore, fourth fluorophore, fifth fluorophore, and sixth fluorophore.

According to aspects of the present disclosure, the first fluorophore and the second fluorophore have distinguishable excitation maxima and emission maxima, the third fluorophore and the fourth fluorophore have distinguishable excitation maxima and emission maxima, and the fifth fluorophore and the sixth fluorophore have distinguishable excitation maxima and emission maxima. Optionally, a seventh fluorophore included in a control hydrolysis probe has an excitation maximum and emission maximum distinguishable from the first fluorophore and the second fluorophore. Optionally, a seventh fluorophore included in a control hydrolysis probe has an excitation maximum and emission maximum distinguishable from the third fluorophore and the fourth fluorophore. Optionally, a seventh fluorophore included in a control hydrolysis probe has an excitation maximum and emission maximum distinguishable from the fifth fluorophore and the sixth fluorophore.

According to aspects of the present disclosure, each of the first fluorophore, second fluorophore, third fluorophore, fourth fluorophore, fifth fluorophore, and sixth fluorophore have detectably different excitation maxima and emission maxima. Optionally, a seventh fluorophore included in a control hydrolysis probe has an excitation maximum and an emission maximum distinguishable from each of the first fluorophore, second fluorophore, third fluorophore, fourth fluorophore, fifth fluorophore, and sixth fluorophore.

Methods described herein involve detection of fluorophores. Any of a variety of fluorophores and their complementary detection modalities can be used when practicing the described methods, such as a fluorometer, flow cytometer, luminometer, or fluorescence detection microscope.

According to aspects of the present disclosure, the reaction mixture or each individual reaction mixture, includes a thermostable polymerase which has 5'→3' exonuclease activity. According to aspects of the present disclosure, the reaction mixture or each individual reaction mixture, includes a thermostable polymerase which has 5'→3' exonuclease activity, wherein the thermostable polymerase is a Taq polymerase or Tth polymerase.

As disclosed herein, a method of detecting intact SARS-CoV-2 in a test sample including or suspected of including SARS-CoV-2, is highly sensitive and highly specific, such that, even if nucleic acids of another organism are present in the test sample, the method specifically detects the SARS-CoV-2 nucleic acids. As disclosed herein, a method of detecting intact SARS-CoV-2 in a test sample including or suspected of including SARS-CoV-2, is highly sensitive and highly specific, such that, even if human nucleic acids are present in a test sample obtained from, or derived from, a human, they are not amplified and the method specifically detects the SARS-CoV-2 nucleic acids.

As disclosed herein, a method of detecting intact SARS-CoV-2 in a test sample including or suspected of including SARS-CoV-2, is highly sensitive and highly specific, such that, even if nucleic acids of coronaviruses other than SARS-CoV-2 are present, they are not amplified and the method specifically detects the SARS-CoV-2 nucleic acids.

According to aspects of the present disclosure, a method of detecting intact SARS-CoV-2 in a test sample including or suspected of including SARS-CoV-2, includes a control. According to aspects of the present disclosure, a control is a reaction mixture missing a component required for production of an amplification product, such as a reaction mixture without nucleic acids, without amplification reagents, without reverse transcription reagents, without amplification primers, without hydrolysis probes, without a polymerase, or without any two or more thereof.

According to aspects of the present disclosure, a control is a reaction mixture including a non-SARS-CoV-2 nucleic acid. According to aspects of the present disclosure, a control is a reaction mixture including a non-SARS-CoV-2 nucleic acid reaction mixture which includes a control hydrolysis probe and a pair of control primers, wherein the control hydrolysis probe and control primers are specific for the non-SARS-CoV-2 nucleic acid, and wherein the control hydrolysis probe includes a control fluorophore and a quencher of the control fluorophore.

According to aspects of the present disclosure, a control is a reaction mixture including a human nucleic acid. According to aspects of the present disclosure, a control is a reaction mixture including a human nucleic acid reaction mixture which includes a control hydrolysis probe and a pair of control primers, wherein the control hydrolysis probe and control primers are specific for the human nucleic acid, and wherein the control hydrolysis probe includes a control fluorophore and a quencher of the control fluorophore. The control may be present in the same reaction mixture which includes primers and hydrolysis probes specific for a SARS-CoV-2 nucleic acid, or may be in a separate reaction mixture.

According to aspects of the present disclosure, a control is a reaction mixture including a human ribonuclease P protein subunit p30 (RPP30) nucleic acid. According to aspects of the present disclosure, a control is a reaction mixture including a human RPP30 nucleic acid reaction mixture which includes a control hydrolysis probe and a pair of control primers, wherein the control hydrolysis probe and control primers are specific for the human RPP30 nucleic acid, and wherein the control hydrolysis probe includes a control fluorophore and a quencher of the control fluorophore.

Diagnosis

According to aspects of the present disclosure, methods of diagnosing a health condition of a subject are provided including detecting a target nucleic acid in a test sample and determining that the test sample contains the target nucleic acid when the Ct value for all of the fluorophores is positive and less than a predetermined value as described herein.

The health condition can be any health condition characterized by presence or absence of a target nucleic acid in a sample obtained from, or derived from, the subject. Such health conditions include, but are not limited to, viral infection; bacterial infection; fungal infection; mycoplasma infection; abnormal cell proliferation such as pre-neoplastic hyperproliferation, cancer in-situ, neoplasms and metastasis; genetic abnormalities; and genetic variants.

According to aspects of the present disclosure, methods of detecting intact severe acute respiratory syndrome coronavirus 2 (SARS-CoV-2) in a test sample, the test sample including or suspected of including SARS-CoV-2, are provided wherein determining that the test sample contains SARS-CoV-2 when the Ct value for all of the fluorophores is positive and less than a predetermined value provides a diagnosis of positive for infection by SARS-CoV-2.

According to aspects of the present disclosure, methods of detecting intact severe acute respiratory syndrome coronavirus 2 (SARS-CoV-2) in a test sample derived from a human subject, the test sample including or suspected of including SARS-CoV-2, are provided wherein determining that the test sample contains SARS-CoV-2 when the Ct value for all of the fluorophores is positive and less than a predetermined value provides a diagnosis of the human subject as positive for infection by SARS-CoV-2 and therefore having COVID-19.

According to aspects of the present disclosure, a subject diagnosed with a health condition is treated with an effective amount of one or more therapeutic agents.

According to aspects of the present disclosure, a subject diagnosed as positive for infection by SARS-CoV-2 is treated with an effective amount of one or more therapeutic agents.

The term "therapeutic agent" is used herein to refer to a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Therapeutic agents included according to aspects of methods and compositions of the present invention include, but are not limited to, antibiotics, antivirals, antineoplastic agents, analgesics, antipyretics, antihistamines, anti-osteoporosis agents, anti-osteonecrosis agents, antiinflammatory agents, anxiolytics, vasopressors, growth factors, hormones, non-steroidal anti-inflammatory agents, steroids, and vasoactive agents.

Therapeutic agents are described, for example, in Goodman et al., Goodman and Gilman's The Pharmacological Basis of Therapeutics, 8th Ed., Macmillan Publishing Co., 1990.

Compositions and Commercial Packages

Compositions and commercial packages are provided according to aspects of the disclosure for detecting a target nucleic acid in a test sample including or suspected of including the target nucleic acid. In such a composition and/or commercial package, one or more hydrolysis probes and/or amplification primers is provided.

Fluorophores are selected for inclusion in hydrolysis probes included in a composition and/or commercial package according to aspects of the present disclosure based on characteristics including, but not limited to, excitation maximum wavelength and emission maximum wavelength, as disclosed herein.

Compositions and/or commercial packages are provided according to aspects of the disclosure for detecting a target nucleic acid in a test sample including or suspected of including the target nucleic acid which include at least one, at least two, at least three, or more, sets of amplification primers and hydrolysis probes specific for the target nucleic acid selected from: 1) a first set including: a first hydrolysis probe specific for the target nucleic acid, a second hydrolysis probe specific for the target nucleic acid, and a first pair of amplification primers specific for the target nucleic acid, wherein the first hydrolysis probe comprises a first fluorophore and a quencher of the first fluorophore, wherein the second hydrolysis probe comprises a second fluorophore and a quencher of the second fluorophore and wherein the first hydrolysis probe and the second hydrolysis probe are specific for an amplification product of the first pair of amplification primers; 2) a second set of amplification primers and hydrolysis probes specific for the target nucleic acid, the second set including: a third hydrolysis probe specific for the target nucleic acid, a fourth hydrolysis probe specific for the target nucleic acid, and a second set of amplification primers specific for the target nucleic acid, wherein the third hydrolysis probe comprises a third fluorophore and a quencher of the third fluorophore, wherein the fourth hydrolysis probe comprises a fourth fluorophore and a quencher of the fourth fluorophore, and wherein the third hydrolysis probe and the fourth hydrolysis probe are specific for an amplification product of the second pair of amplification primers; and 3) a third set of amplification primers and hydrolysis probes specific for the target nucleic acid, the third set including: a fifth hydrolysis probe specific for the target nucleic acid, a sixth hydrolysis probe specific for the target nucleic acid, and a third pair of amplification primers specific for the target nucleic acid, wherein the fifth hydrolysis probe comprises a fifth fluorophore and a quencher of the fifth fluorophore, wherein the sixth hydrolysis probe comprises a sixth fluorophore and a quencher of the sixth fluorophore, and wherein the fifth hydrolysis probe and the sixth hydrolysis probe are specific for an amplification product of the third pair of amplification primers.

According to aspects of the present disclosure, the first fluorophore and the second fluorophore have detectably different emission maxima, different excitation maxima, or the same emission maxima and excitation maxima, the third fluorophore and the fourth fluorophore have detectably different emission maxima, different excitation maxima, or the same emission maxima and excitation maxima, and the fifth fluorophore and the sixth fluorophore have detectably different emission maxima, different excitation maxima, or the same emission maxima and excitation maxima.

Optionally, control primers and/or a control hydrolysis probe are included in a composition and/or commercial package according to aspects of the present disclosure.

Optionally, a control hydrolysis probe is included in a composition and/or commercial package according to aspects of the present disclosure wherein the control hydrolysis probe includes a seventh fluorophore which has an excitation maximum and an emission maximum distinguishable from each of the first fluorophore, second fluorophore, third fluorophore, fourth fluorophore, fifth fluorophore, and sixth fluorophore or which has an excitation maximum and/or an emission maximum which is not distinguishable from at least one of the first fluorophore, second fluorophore, third fluorophore, fourth fluorophore, fifth fluorophore, and sixth fluorophore, or which has an excitation maximum and/or an emission maximum which is not distinguishable from any of: the first fluorophore, second fluorophore, third fluorophore, fourth fluorophore, fifth fluorophore, and sixth fluorophore.

Compositions and/or commercial packages are provided according to aspects of the disclosure which include one or more reverse transcription reagents, one or more hybridization reagents, and/or one or more PCR reagents, such as, but not limited to, a reverse transcriptase, a thermostable polymerase with 5'→3' exonuclease activity, and/or a hybridization and/or polymerase buffer.

Compositions and/or commercial packages are provided according to aspects of the disclosure which include one or more ancillary components, such as a buffer or diluent.

Compositions and/or commercial packages are provided according to aspects of the disclosure for detecting intact severe acute respiratory syndrome coronavirus 2 (SARS-CoV-2) in a test sample including or suspected of including SARS-CoV-2. In such a kit, one or more hydrolysis probes and/or amplification primers is provided.

Compositions and/or commercial packages are provided according to aspects of the disclosure which include at least one, at least two, or all three, sets of amplification primers and hydrolysis probes selected from: 1) a first set including: a first hydrolysis probe including SEQ ID NO:3, a second hydrolysis probe including SEQ ID NO:4, and primers including SEQ ID NO:1 and SEQ ID NO:2, wherein the first hydrolysis probe comprises a first fluorophore and a quencher of the first fluorophore, and wherein the second hydrolysis probe comprises a second fluorophore and a quencher of the second fluorophore; 2) a second set of amplification primers and hydrolysis probes, the second set including: a third hydrolysis probe including SEQ ID NO:7, a fourth hydrolysis probe including SEQ ID NO:8, and primers including SEQ ID NO:5 and SEQ ID NO:6, wherein the third hydrolysis probe comprises a third fluorophore and a quencher of the third fluorophore, and wherein the fourth hydrolysis probe comprises a fourth fluorophore and a quencher of the fourth fluorophore; and 3) a third set of amplification primers and hydrolysis probes, the third set including: a fifth hydrolysis probe including SEQ ID NO:11, a sixth hydrolysis probe including SEQ ID NO:12, and primers including SEQ ID NO:9 and SEQ ID NO:10, wherein the fifth hydrolysis probe comprises a fifth fluorophore and a quencher of the fifth fluorophore, and wherein the sixth hydrolysis probe comprises a sixth fluorophore and a quencher of the sixth fluorophore.

Optionally, a seventh fluorophore included in a control hydrolysis probe is included in a commercial package according to aspects of the present disclosure which has an excitation maximum and an emission maximum distinguishable from each of the first fluorophore, second fluorophore, third fluorophore, fourth fluorophore, fifth fluorophore, and sixth fluorophore or which has an excitation maximum and/or an emission maximum which is not distinguishable from at least one of the first fluorophore, second fluorophore, third fluorophore, fourth fluorophore, fifth fluorophore, and sixth fluorophore, or which has an excitation maximum and/or an emission maximum which is not distinguishable from any of the first fluorophore, second fluorophore, third fluorophore, fourth fluorophore, fifth fluorophore, and sixth fluorophore.

Compositions and/or commercial packages are provided according to aspects of the disclosure which include at least one, at least two, or all three, sets of amplification primers and hydrolysis probes selected from: 1) a first set including: a first hydrolysis probe including SEQ ID NO:3, a second hydrolysis probe including SEQ ID NO:4, and primers including SEQ ID NO:1 and SEQ ID NO:2, wherein the first hydrolysis probe comprises a first fluorophore and a quencher of the first fluorophore, and wherein the second hydrolysis probe comprises a second fluorophore and a quencher of the second fluorophore; 2) a second set of amplification primers and hydrolysis probes, the second set including: a third hydrolysis probe including SEQ ID NO:7, a fourth hydrolysis probe including SEQ ID NO:8, and primers including SEQ ID NO:5 and SEQ ID NO:6, wherein the third hydrolysis probe comprises a third fluorophore and a quencher of the third fluorophore, and wherein the fourth hydrolysis probe comprises a fourth fluorophore and a quencher of the fourth fluorophore; and 3) a third set of amplification primers and hydrolysis probes, the third set including: a fifth hydrolysis probe including SEQ ID NO:11, a sixth hydrolysis probe including SEQ ID NO:12, and primers including SEQ ID NO:9 and SEQ ID NO:10, wherein the fifth hydrolysis probe comprises a fifth fluorophore and a quencher of the fifth fluorophore, and wherein the sixth hydrolysis probe comprises a sixth fluorophore and a quencher of the sixth fluorophore, wherein the first fluorophore and the second fluorophore have detectably different emission maxima, different excitation maxima, or the same emission maxima and excitation maxima, wherein the third fluorophore and the fourth fluorophore have detectably different emission maxima, different excitation maxima, or the same emission maxima and excitation maxima, wherein the fifth fluorophore and the sixth fluorophore have detectably different emission maxima, different excitation maxima, or the same emission maxima and excitation maxima.

Optionally, a seventh fluorophore included in a control hydrolysis probe has an excitation maximum and an emission maximum distinguishable from each of the first fluorophore, second fluorophore, third fluorophore, fourth fluorophore, fifth fluorophore, and sixth fluorophore or has the same excitation maximum and an emission maximum as any one of the first fluorophore, second fluorophore, third fluorophore, fourth fluorophore, fifth fluorophore, and sixth fluorophore, or the same as all of the first fluorophore, second fluorophore, third fluorophore, fourth fluorophore, fifth fluorophore, and sixth fluorophore.

As detailed hereinabove, according to aspects of the present disclosure, each of the first fluorophore, second fluorophore, third fluorophore, fourth fluorophore, fifth fluorophore, and sixth fluorophore included in hydrolysis probes in commercial packages have detectably different emission maxima, different excitation maxima, or the same emission maxima and excitation maxima. Optionally, a seventh fluorophore included in a control hydrolysis probe is included in a composition and/or commercial package according to aspects of the present disclosure which has an excitation maximum and an emission maximum distinguishable from each of the first fluorophore, second fluorophore, third fluorophore, fourth fluorophore, fifth fluorophore, and sixth fluorophore.

Compositions and/or commercial packages according to aspects of the present disclosure are provided wherein the first fluorophore is FAM or HEX, the second fluorophore is FAM or HEX but not identical to the first fluorophore, the quencher of the first fluorophore is Black Hole Quencher 1 (BHQ1), and the quencher of the second fluorophore is BHQ1; the third fluorophore is FAM or HEX, the fourth fluorophore is FAM or HEX but not identical to the third fluorophore, the quencher of the third fluorophore is BHQ1, and the quencher of the fourth fluorophore is BHQ1; and the fifth fluorophore is FAM or HEX, the sixth fluorophore is FAM or HEX but not identical to the fifth fluorophore, the quencher of the fifth fluorophore is BHQ1, and the quencher of the sixth fluorophore is BHQ1. Optionally, a seventh fluorophore included in a control hydrolysis probe wherein the seventh fluorophore is FAM or HEX, and the quencher of the seventh fluorophore is BHQ1.

Optionally, a reverse transcriptase is included in a composition and/or commercial package according to aspects of the present disclosure.

Embodiments of inventive compositions and methods are illustrated in the following examples. These examples are provided for illustrative purposes and are not considered limitations on the scope of inventive compositions and methods.

EXAMPLES

Primer and Probe Design

GenBank sequence MN908947 and Reference sequence NC-45512.2 were used for SARS-CoV-2 genome sequence analysis and assay design. Primers and probes for sets A, B and C were designed such that each oligonucleotide has 100% identity to SARS-CoV-2 genome and targets the nucleocapsid phosphoprotein gene at the 3' end of the viral RNA.

To ensure ultra-specificity to SARS-CoV-2 genome, primers and probes sequences were compared against all nucleic acids sequences present in the NCBI repository using BLAST, and were then further organism-filtered against all human nucleic acid sequences and the genomes of the other common cold-causing coronaviruses 229E, NL63, OC43 or HKU1.

Primers and probes sequences of the present disclosure for the distinct sets recognized only SARS-CoV-2 sequences with 100% identity in over 100 distinct SARS-CoV-2 viral genomes, and organism-filtered blastn results showed that no significant similarity was found against human genome and/or transcriptome sequences.

Blastn analysis for Set A forward primer. NCBI's blastn alignment was used to conduct sequence identity analysis for Set A forward primer against all nucleic acid sequences present at NCBI repository. Results indicate that forward primer for Set A has 100% identity to only SARS-CoV-2 coronavirus genome sequences. Blastn sequence alignment analysis for Set A forward primer. Sequence alignment analysis demonstrates that Set A forward primer aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set A reverse primer. NCBI's blastn alignment was used to conduct sequence identity analysis for Set A reverse primer against all nucleic acid sequences present at NCBI repository. Results indicate that reverse primer for Set A has 100% identity to only SARS-CoV-2 coronavirus genome sequences. Blastn sequence alignment analysis for Set A reverse primer. Sequence alignment analysis demonstrates that Set A reverse primer aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set A FAM probe. NCBI's blastn alignment was used to conduct sequence identity analysis for Set A FAM probe against all nucleic acid sequences present at NCBI repository. Results indicate that FAM probe for Set A has 100% identity to only SARS-CoV-2 coronavirus genome sequences. Sequence alignment analysis demonstrates that Set A FAM probe aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set A HEX probe. NCBI's blastn alignment was used to conduct sequence identity analysis for Set A HEX probe against all nucleic acid sequences present at NCBI repository. Results indicate that HEX probe for Set A has 100% identity to only SARS-CoV-2 coronavirus genome sequences. Sequence alignment analysis demonstrates that Set A HEX probe aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set B forward primer. NCBI's blastn alignment was used to conduct sequence identity analysis for Set B forward primer against all nucleic acid sequences present at NCBI repository. Results indicate that forward primer for Set B has 100% identity to only SARS-CoV-2 coronavirus genome sequences. Blastn sequence alignment analysis for Set B forward primer. Sequence alignment analysis demonstrates that Set B forward primer aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set B reverse primer. NCBI's blastn alignment was used to conduct sequence identity analysis for Set B reverse primer against all nucleic acid sequences present at NCBI repository. Results indicate that reverse primer for Set B has 100% identity to only SARS-CoV-2 coronavirus genome sequences. Blastn sequence alignment analysis for Set B reverse primer. Sequence alignment analysis demonstrates that Set B reverse primer aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set B FAM probe. NCBI's blastn alignment was used to conduct sequence identity analysis for Set B FAM probe against all nucleic acid sequences present at NCBI repository. Results indicate that FAM probe for Set B has 100% identity to only SARS-CoV-2 coronavirus genome sequences. Sequence alignment analysis demonstrates that Set B FAM probe aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set B HEX probe. NCBI's blastn alignment was used to conduct sequence identity analysis for Set B HEX probe against all nucleic acid sequences present at NCBI repository. Results indicate that HEX probe for Set B has 100% identity to only SARS-CoV-2 coronavirus genome sequences. Sequence alignment analysis demonstrates that Set B HEX probe aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set C forward primer. NCBI's blastn alignment was used to conduct sequence identity analysis for Set C forward primer against all nucleic acid sequences present at NCBI repository. Results indicate that forward primer for Set C has 100% identity to only SARS-CoV-2 coronavirus genome sequences. Blastn sequence alignment analysis for Set C forward primer. Sequence alignment analysis demonstrates that Set C forward primer aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set C reverse primer. NCBI's blastn alignment was used to conduct sequence identity analysis for Set C reverse primer against all nucleic acid sequences present at NCBI repository. Results indicate that reverse primer for Set C has 100% identity to only SARS-CoV-2 coronavirus genome sequences. Blastn sequence alignment analysis for Set C reverse primer. Sequence alignment analysis demonstrates that Set C reverse primer aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set C FAM probe. NCBI's blastn alignment was used to conduct sequence identity analysis for Set C FAM probe against all nucleic acid sequences present at NCBI repository. Results indicate that FAM probe for Set C has 100% identity to only SARS-CoV-2 coronavirus genome sequences. Sequence alignment analysis demonstrates that Set C FAM probe aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Blastn analysis for Set C HEX probe. NCBI's blastn alignment was used to conduct sequence identity analysis for Set C HEX probe against all nucleic acid sequences present at NCBI repository. Results indicate that HEX probe for Set C has 100% identity to only SARS-CoV-2 coronavirus genome sequences. Sequence alignment analysis demonstrates that Set C HEX probe aligns with 100% identity to 100 distinct SARS-CoV-2 genomes. Blastn sequence alignment was conducted against all nucleic acid sequences present at NCBI repository and the results were subsequently organism-filtered for human nucleic acid sequences as well as for genome sequences from the other common cold-causing coronavirus 229E, NL63, OC43 and HKU1. Blastn results indicate "No significant similarity found."

Design of an assay according to aspects of the present disclosure includes use of two, non-overlapping, hydrolysis-based probes per amplicon with fluorescence signals, on distinguishable regions of the light spectrum. Given that hydrolysis probe-based qPCR specificity is attained through the inclusion and use of highly-specific hybridizing probes, an assay according to aspects of the present disclosure uses two fluorescent probes per primer pair, corresponding to the negative and positive strands of the generated amplicon and further recognizing two non-overlapping sequences of the amplicon, thus allowing concordant and ultra-specific detection of a target nucleic acid.

SARS-CoV-2 specific probes were 5' modified with FAM or HEX fluorophores and carried the Förster resonance energy transfer (FRET) quencher BHQ1 at the 3' end for background-noise cancellation.

For detection of human RNA, two alternative RPP30 gene Sets were used whose single probe was labeled with Cy5 at 5' end and carried FRET quencher BHQ3 at the 3' end.

```
Primers and probes sequences for Set A are:
Forward primer
                                              (SEQ ID NO: 1)
5'-GTGGACCCTCAGATTCAACTGG Reverse primer
                                              (SEQ ID NO: 2)
5'-TGAGAGCGGTGAACCAAGACG Probe1
                                              (SEQ ID NO: 3)
5'-FAM-GTAACCAGAATGGAGAACGCAGTGG-BHQ1

Probe2
                                              (SEQ ID NO: 4)
5'-HEX-GGTAAACCTTGGGGCCGACGTTG-BHQ1

Primers and probes sequences for Set B are:
Forward primer
                                              (SEQ ID NO: 5)
5'-CTGCTAACAATGCTGCAATCGTGC Reverse primer
                                              (SEQ ID NO: 6)
5'-CTGTTGCGACTACGTGATGAGG Probe1
                                              (SEQ ID NO: 7)
5'-FAM-GCTTCTACGCAGAAGGGAGCAGAG-BHQ1

Probe2
                                              (SEQ ID NO: 8)
5'-HEX-CGAGAAGAGGCTTGACTGCCG-BHQ1

Primers and probes sequences for Set C are:
Forward primer
                                              (SEQ ID NO: 9)
5'-GCTCTCACTCAACATGGCAAGG Reverse primer
                                              (SEQ ID NO: 10)
5'-CGAATTCGTCTGGTAGCTCTTCG Probe1
                                              (SEQ ID NO: 11)
5'-FAM-CCTCGAGGACAAGGCGTTCCAA-BHQ1

Probe2
                                              (SEQ ID NO: 12)
5'-HEX-GGTCATCTGGACTGCTATTGGTGTT-BHQ1

Primers and probe sequences for first control
RPP30 Set:
Forward primer
                                              (SEQ ID NO: 13)
5'-CAGATTTGGACCTGCGAGC Reverse primer
                                              (SEQ ID NO: 14)
5'-AGCGGCTGTCTCCACAAGTC Probe
                                              (SEQ ID NO: 15)
5'-Cy5-TTCTGACCTGAAGGCTCTGCGCG-BHQ3

Primers and probe sequences used for second
control RPP30 Set:
Forward primer
                                              (SEQ ID NO: 13)
5'-CAGATTTGGACCTGCGAGC Reverse primer
                                              (SEQ ID NO: 16)
5'-GATTGATAGCAACAACTGAATAGCC Additional probe
                                              (SEQ ID NO: 17)
5'-Cy5- GCGGCTGTCTCCACAAGTCC-BHQ3
```

RT-qPCR Reagents and Parameters

RT-qPCR detection of SARS-CoV-2 genome utilizes one-step RT-qPCR using highly-reliable, UltraPure (UP) Array-Script reverse transcriptase and high-yield, time release AmpliTaq Gold DNA Polymerase.

A synthetic, in vitro transcribed and ultrapure DNA-free (DNase-treated) RNA fragment containing a segment of SARS-CoV-2 nucleocapsid gene was used for molecular detection assays in a serial-dilution range from 2 copies/µL to $2\times10^6$ copies/µL. Primers and probes for each of the primer/probe Sets were prepared as a 20× stock in nuclease-free water and were used at a final concentration of 1 µM for primers and 250 nM for probes (4:1 ratio), and a total of 5 µL of sample was used in each reaction for detection ranging from 10 to $10\times10^7$ RNA molecules per reaction.

Sample RNA was prepared by preparing serial dilutions of SARS-CoV-2 target RNA at the above-mentioned concentrations in a human RNA solution containing 20 ng/µL of total human, DNA-free (in-column DNase treated), RNA.

The 2×PCR Master mix solution contains ROX, so that this fluorophore is thus readily available for qPCR instrumentation requiring ROX normalization.

The RT-qPCR reaction for a single, 13 μL reaction is as follows:
2×PCR Master mix 6.5 μL
40×RT enzyme mix 0.325 μL
Primers/probes mix 0.65 μL
$H_2O$ 0.525 μL
Sample 5.0 μL A pre-reaction reaction mix (without sample), is prepared according to the total number of samples to be assayed and their pertinent replicates.

RT step and qPCR cycling parameters for a total of 40 cycles are as follows:
1. 48° C. for 15 minutes
2. 95° C. for 10 minutes
3. 95° C. for 15 seconds
4. 60° C. for 60 seconds
5. Fluorescence interrogation
6. Go to step 3 for 39 times.

Outcome analysis is done through CT assessment, in replicates, between each pair of signals (FAM and HEX) for a given set, and through evaluation of positivity throughout bi-conditional logical connectives analysis: If and only if both CT values yield a positive and valid number (less than 40) for amplification and quantification result then the outcome of the reacting set is considered positive. Further, if any two of three or all three SARS-COV-2 primer/probe Sets score positive for SARS-COV-2 presence then the sample is likewise considered positive for Covid-19.

Methods for SARS-CoV-2 according to aspects of the present disclosure detect as little as 1 copy/μL of SARS-CoV-2 virus per sample.

EXAMPLES

One Set:
Detection using primers/probes Set A and indicating effective amplification and detection of SARS-CoV-2 nucleocapsid RNA in HEX channel and detection using primers/probes Set A and indicating effective amplification and detection of SARS-CoV-2 nucleocapsid RNA in FAM channel.

Detection using primers/probes Set B and indicating effective amplification and detection of SARS-CoV-2 nucleocapsid RNA in HEX channel and detection using primers/probes Set B and indicating effective amplification and detection of SARS-CoV-2 nucleocapsid RNA in FAM channel.

Detection using primers/probes Set C and indicating effective amplification and detection of SARS-CoV-2 nucleocapsid RNA in HEX channel and detection using primers/probes Set C and indicating effective amplification and detection of SARS-CoV-2 nucleocapsid RNA in FAM channel.

Two Sets:
Detection using primers/probes Set A and indicating effective amplification and detection of SARS-CoV-2 nucleocapsid RNA in HEX channel and detection using primers/probes Set A and indicating effective amplification and detection of SARS-CoV-2 nucleocapsid RNA in FAM channel, and detection using primers/probes Set B and indicating effective amplification and detection of SARS-CoV-2 nucleocapsid RNA in HEX channel and detection using primers/probes Set B and indicating effective amplification and detection of SARS-CoV-2 nucleocapsid RNA in FAM channel.

Detection using primers/probes Set A and indicating effective amplification and detection of SARS-CoV-2 nucleocapsid RNA in HEX channel and detection using primers/probes Set A and indicating effective amplification and detection of SARS-CoV-2 nucleocapsid RNA in FAM channel, and detection using primers/probes Set C and indicating effective amplification and detection of SARS-CoV-2 nucleocapsid RNA in HEX channel and detection using primers/probes Set C and indicating effective amplification and detection of SARS-CoV-2 nucleocapsid RNA in FAM channel.

Detection using primers/probes Set B and indicating effective amplification and detection of SARS-CoV-2 nucleocapsid RNA in HEX channel and detection using primers/probes Set B and indicating effective amplification and detection of SARS-CoV-2 nucleocapsid RNA in FAM channel, and detection using primers/probes Set C and indicating effective amplification and detection of SARS-CoV-2 nucleocapsid RNA in HEX channel and detection using primers/probes Set C and indicating effective amplification and detection of SARS-CoV-2 nucleocapsid RNA in FAM channel.

Three Sets:
Detection using primers/probes Set A and indicating effective amplification and detection of SARS-CoV-2 nucleocapsid RNA in HEX channel and detection using primers/probes Set A and indicating effective amplification and detection of SARS-CoV-2 nucleocapsid RNA in FAM channel, and detection using primers/probes Set B and indicating effective amplification and detection of SARS-CoV-2 nucleocapsid RNA in HEX channel and detection using primers/probes Set B and indicating effective amplification and detection of SARS-CoV-2 nucleocapsid RNA in FAM channel, and detection using primers/probes Set C and indicating effective amplification and detection of SARS-CoV-2 nucleocapsid RNA in HEX channel and detection using primers/probes Set C and indicating effective amplification and detection of SARS-CoV-2 nucleocapsid RNA in FAM channel.

Clinical Validation
Methods: 20 presumptive positive and 20 presumptive negative samples (determined by Detroit Medical Center Clinical Microbiology Laboratory) were used for comparative analysis with methods according to the present disclosure. Swab samples in transport media were used to isolate DNA-free RNA. Samples were mixed 1:3 with Direct-zol (Trizol) reagent (Zymo research), mixed with chloroform (1/5 of the sample/Direct-zol combined volume) and spun for at 4° C. for 15 min at 10,000 g. The supernatant was carefully removed and mixed 1:1 with 100% ethanol and, following manufacturer (Zymo Research) instructions, loaded into the binding spin column. In-column DNase treatment was done as indicated by the kit's manufacturer (Zymo Research) and the resulting ultrapure, DNA-free RNA was eluted in 65 μL of nuclease-free water. These DNA-free RNA samples were used for subsequent RT-qPCR analysis. The 20 presumptive negative samples were determined also as negative using methods of the present disclosure, and 18 of the 20 presumptive positive samples were determined as positive by our novel ultra-precision platform. The two presumptive positive samples that were determine as negative using methods according to aspects of the present disclosure were further tested with the WHO system used as a resolver test, whose outcome was also negative and, hence, confirmed the negative results obtained by methods of the present disclosure.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of detecting intact severe acute respiratory syndrome coronavirus 2 (SARS-CoV-2) in a test sample comprising or suspected of comprising SARS-CoV-2, the method comprising:
detecting the presence of a SARS-CoV-2 nucleic acid encoding nucleocapsid phosphoprotein in the test sample by reverse-transcription quantitative polymerase chain reaction (RT-qPCR), wherein the RT-qPCR comprises: forming a reaction mixture comprising the test sample, nucleic acid amplification reagents, and one, two, or three of i), ii), and iii):
i) a first set of amplification primers and hydrolysis probes, the first set comprising: a first hydrolysis probe comprising SEQ ID NO:3, a second hydrolysis probe comprising SEQ ID NO:4, and amplification primers comprising SEQ ID NO:1 and SEQ ID NO:2, wherein the first hydrolysis probe comprises a first fluorophore and a quencher of the first fluorophore, wherein the second hydrolysis probe comprises a second fluorophore and a quencher of the second fluorophore, and wherein the first hydrolysis probe and the second hydrolysis probe are specific for an amplification product of the amplification primers;
ii) a second set of amplification primers and hydrolysis probes, the second set comprising: a third hydrolysis probe comprising SEQ ID NO:7, a fourth hydrolysis probe comprising SEQ ID NO:8, and amplification primers comprising SEQ ID NO:5 and SEQ ID NO:6, wherein the third hydrolysis probe comprises a third fluorophore and a quencher of the third fluorophore, wherein the fourth hydrolysis probe comprises a fourth fluorophore and a quencher of the fourth fluorophore, and wherein the third hydrolysis probe and the fourth hydrolysis probe are specific for an amplification product of the second pair of amplification primers; and
iii) a third set of amplification primers and hydrolysis probes, the third set comprising: a fifth hydrolysis probe comprising SEQ ID NO:11, a sixth hydrolysis probe comprising SEQ ID NO:12, and amplification primers comprising SEQ ID NO:9 and SEQ ID NO:10, wherein the fifth hydrolysis probe comprises a fifth fluorophore and a quencher of the fifth fluorophore, wherein the sixth hydrolysis probe comprises a sixth fluorophore and a quencher of the sixth fluorophore, and wherein the fifth hydrolysis probe and the sixth hydrolysis probe are specific for an amplification product of the third pair of amplification primers;
reacting the reaction mixture under amplification conditions, producing one, two, or more of: first, second, and third amplification products when the SARS-CoV-2 nucleic acid encoding nucleocapsid phosphoprotein is present in the test sample, wherein detectable signals are generated by the fluorophores released from the hydrolysis probes;
detecting the detectable signals of the amplification products;
calculating a cycle threshold (Ct) value for fluorophores while reacting the reaction mixture; and
determining that the test sample contains SARS-CoV-2 when the Ct value for all of the fluorophores is positive, and none is negative, and less than a predetermined value.

2. The method of claim 1, wherein each of the first fluorophore, second fluorophore, third fluorophore, fourth fluorophore, fifth fluorophore, and sixth fluorophore, are detectably different.

3. The method of claim 1, further comprising a control.

4. The method of claim 1, wherein the reaction mixture further comprises at least one control hydrolysis probe, and a pair of control primers, wherein the control hydrolysis probe and control primers are specific for a non-target nucleic acid, wherein the control hydrolysis probe comprises a control fluorophore and a quencher of the control fluorophore.

5. The method of claim 1, wherein the control comprises:
forming a further reaction mixture, the further reaction mixture comprising the test sample, nucleic acid amplification reagents, at least one control hydrolysis probe, and a pair of control primers, wherein the control hydrolysis probe and control primers are specific for a non-target nucleic acid, wherein the control hydrolysis probe comprises a control fluorophore and a quencher of the control fluorophore.

* * * * *